(12) United States Patent
Gould-Rothberg

(10) Patent No.: US 6,551,812 B1
(45) Date of Patent: Apr. 22, 2003

(54) COMPOSITIONS AND METHODS RELATING TO THE PEROXISOMAL PROLIFERATOR ACTIVATED RECEPTOR-α MEDIATED PATHWAY

(75) Inventor: Bonnie Gould-Rothberg, New Haven, CT (US)

(73) Assignee: CuraGen Corporation, New Haven, CT (US)

(*) Notice: Subject to any disclaimer, the term of this patent is extended or adjusted under 35 U.S.C. 154(b) by 0 days.

(21) Appl. No.: 09/440,315

(22) Filed: Nov. 12, 1999

Related U.S. Application Data

(60) Provisional application No. 60/108,293, filed on Nov. 13, 1998, and provisional application No. 60/126,465, filed on Mar. 26, 1999.

(51) Int. Cl.[7] .................. C12N 5/00; G01N 33/566; C07H 19/00; C07H 21/00
(52) U.S. Cl. .............. 435/240.2; 435/240.21; 436/501; 536/22.1
(58) Field of Search ............. 436/501; 435/240.2, 435/240.21; 536/22.1

(56) References Cited

U.S. PATENT DOCUMENTS 5,356,807 A * 10/1994 Blass et al. ............ 435/240.2

FOREIGN PATENT DOCUMENTS

| WO | WO 96/01317 | 1/1996 |
| WO | WO 98/27994 | 7/1998 |
| WO | WO 99/05161 | 2/1999 |

OTHER PUBLICATIONS

International Search Report, PCT/US99/26737.
Aoyama et al. "Altered Constituitive Expression of Fatty Acid–Metabolizing Enzymes in Mice Lacking the Peroxisome Proliferator Activated Receptor Alpha" *J. Biol. Chem.* 273 (10):5678–5684 (1998).
Ouali F. et al. "Dietary lipis regulate beta–oxidation enzyme gene expression in developing rat kidney" *Am. J. Physiology* 275 (5):F777–F784. (1988).
Brown, P.J. et al. "A ureido–thioisobutyric acid (GW9578) is a subtype–selective PPAR alpha agonist with potent lipid–lowering activity" *J. Med. Chem.* 42(19):3785–3788 (1999).
Ellinghaus P. et al. "Phytanic acid activates the peroxisome proliferator–activated receptor alpha (PPAR alpha) in sterol carrier protein 2–/sterol carrier protein x–deficient mice" *J. Biol. Chem.* 274(5):2766–2772 (1999).
(1998). "New warnings issued for bromfenac, astemizole [news]." *Am J Health Syst Pharm* 55(6): 526.
Aldridge, T. C., J. D. Tugwood, et al. (1995). "Identification and characterization of DNA elements implicated in the regulation of CYP4A1 transcription." *Biochem J* 306(Pt 2): 473–9.

Alvares, K., A. Carrillo, et al. (1990). "Identification of cytosolic peroxisome proliferator binding protein as a member of the heat shock protein HSP70 family." *Proc Natl Acad Sci U S A* 87(14): 5293–7.
Assimacopoulos–Jeannet, F., M. Moinat, et al. (1991). "Effects of a peroxisome proliferator on beta–oxidation and overall energy balance in obese (fa/fa) rats." *Am J Physiol* 260(2 Pt 2): R278–83.
Austin, E. W., J. R. Okita, et al. (1995). "Modification of lipoperoxidative effects of dichloracetate and trichloroacetate is associated with peroxisome proliferation." *Toxicology* 97(1–3): 59–69.
Baes, M., H. Castelein, et al. (1995). "Antagonism of COUP–TF and PPAR alpha/RXR alpha on the activation of the malic enzyme gene promoter: modulation by 9–cis RA." *Biochem Biophys Res Commun* 215(1): 338–45.
Bars, R. G., D. R. Bell, et al. (1993). "Induction of cytochrome P450 and peroxisomal enzymes by clofibric acid in vivo and in vitro." *Biochem Pharmacol* 45(10): 2045–53.
Bateman, J. B., T. Kojis, et al. (1993). "Mapping of aldose reductase gene sequences to human chromosomes 1, 3, 7, 9, 11, and 13." *Genomics* 17(3): 560–5.
Beil, F. U., A. Schrameyer–Wernecke, et al. (1990). "Lovastatin versus bezafibrate: efficacy, tolerability, and effect on urinary mevalonate." *Cardiology* 77(Suppl 4): 22–32.
Bredie, S. J., H. T. Westerveld, et al. (1996). "Effects of gemfibrozil or simvastatin on apolipoprotein–B–containing lipoproteins, apolipoprotein–CII and lipoprotein(a) in familial combined hyperlipidaemia." *Neth J Med* 49(2): 59–67.
Brenn, T., T. Aoyama, et al. (1996). "Dermal fibroblast culture as a model system for studies of fibrillin assembly and pathogenic mechanisms: defects in distinct groups of individuals with Marfan's syndrome." *Lab Invest* 75(3): 389–402.
Brunner, S., K. Kramer, et al., (1997). "Cloning and characterization of murine carnitine acetyltransferase: evidence for a requirement during cell cycle progression." *Biochem J* 322(Pt 2): 403–10.
Castelein, H., T. Gulick, et al. (1994). "The peroxisome proliferator activated receptor regulates malic enzyme gene expression." *J Biol Chem* 269(43): 26754–8.

(List continued on next page.)

*Primary Examiner*—W. Gary Jones
*Assistant Examiner*—Arun Chakrabarti
(74) *Attorney, Agent, or Firm*—Mintz, Levin, Cohn, Ferris, Glovsky and Popeo, P.C.; Ivor R. Elrifi; Cynthia Kozakiewicz

(57) ABSTRACT

The present invention describes polynucleotides and polypeptides associated with PPARα-mediated pathways that are useful as therapeutic compositions in method for the treatment of peroxisomal disorders. These polynucleotides and polypeptides were identified through the use of differentioal gene expression analysis. In particular, the present invention discloses eleven novel gene fragments, and numerous single nucleotide polymorphisms, located in previously disclosed genes, all of which have been discovered to be associated with PPARα-mediated pathways.

4 Claims, 32 Drawing Sheets

OTHER PUBLICATIONS

Chen, F., S. W. Law, et al. (1993). "Identification of two mPPAR related receptors and evidence for the existence of five subfamily members." *Biochem Biophys Res Commun* 196(2): 671–7.

Choi, S. J., D. H. Oh, et al. (1995). "Molecular cloning and sequences analysis of the rat liver carnitine octanoyltransferase cDNA, its natural gene and the gene promoter." *Biochim Biophys Acta* 1264(2): 215–22.

Christiansen, R. Z., H. Osmundsen, et al. (1978). "The effects of clofibrate feeding on the metabolism of palmitate and erucate in isolated hepatocytes." *Lipids* 13(7): 487–91.

Corton, J. C., C. Bocos, et al. (1996). "Rat 17 beta–hydroxysteroid dehydrogenase type IV is a novel peroxisome proliferator–inducible gene." *Mol Pharmacol* 50(5): 1157–66.

Devchand, P. R., H. Keller, et al. (1996). "The PPARalpha–leukotriene B4 pathway to inflammation control [see comments]." *Nature* 384(6604): 39–43.

Dreyer, C., G. Krey, et al. (1992). "Control of the peroxisomal beta–oxidation pathway by a novel family of nuclear hormone receptors." *Cell* 68(5): 879–87.

Esser, V., C. H. Britton, et al. (1993). "Cloning, sequencing, and expression of a cDNA encoding rat liver carnitine palmitoyltransferase I. Direct evidence that a single polypeptide is involved in inhibitor interaction and catalytic function." *J Biol Chem* 268(8): 5817–22.

Forman, B. M., J. Chen, et al. (1997). "Hypolipidemic drugs, polyunsaturated fatty acids, and eicosanoids are ligands for peroxisome proliferator–activated receptors alpha and delta." *Proc Natl Acad Sci U S A* 94(9): 4312–7.

Foxworthy, P. S. and P. I. Eacho (1988). "Inhibition of hepatic fatty acid oxidation at carnitine palmitoyltransferase I by the peroxisome proliferator 2–hydroxy–3–propyl–4–[6–(tetrazol–5–yl)hexyloxy]acetophenone." *Biochem J* 252(2): 409–14.

Fruchart, J. C., H. B. Brewer, Jr. et al. (1998). "Consensus for the use of fibrates in the treatment of dyslipoproteinemia and coronary heart disease. Fibrate Consensus Group." *Am J. Cardiol* 81(7): 912–7.

Gaw, A., C. J. Packard, et al., (1994). "Effects of ciprofibrate on LDL metabolism in man." *Atherosclerosis* 108(2): 137–48.

Girard, J., D. Perdereau, et al. (1994). "Regulation of lipogenic enzyme gene expression by nutrients and hormones." *Faseb J* 8(1): 36–42.

Grasl–Kraupp, B., T. Waldhor, et al. (1993). "Glutathione S–transferase isoenzyme patterns in different subtypes of enzyme–altered rat liver foci treated with the peroxisome proliferator nafenopin or with phenobarbital." *Carcinogenesis* 14(11): 2407–12.

Gulick, T., S. Cresci, et al. (1994). "The peroxisome proliferator–activated receptor regulates mitochondrial fatty acid oxidative enzyme gene expression." *Proc Natl Acad Sci U S A* 91(23): 11012–6.

Hakkola, E. H., J. K. Hiltunen, et al. (1994). "Mitochondrial 2,4–dienoyl–CoA reductases in the rat: differential responses to clofibrate treatment." *J Lipid Res* 35(10): 1820–8.

Hoogerbrugge, N., L. G. Kerkhofs, et al. (1998). "Gemfibrozil decreases autoantibodies against oxidized low–density lipoprotein in men with combined hyperlipidaemia." *J Intern Med* 243(5): 355–9.

Huang, Q., K. Alvares, et al. (1994). "Association of peroxisome proliferator–activated receptor and Hsp72." *J Biol Chem* 269(11): 8493–7.

Huizing, M., V. Iacobazzi, et al. (1997). "Cloning of the human carnitine–acylcarnitine carrie cDNA and identification of the molecular defect in a patient." *Am J Hum Genet* 61(6): 1239–45.

Indiveri, C., V. Iacobazzi, et al. (1997). "The mitochondrial carnitine carrier protein: cDNA cloning, primary structure and comparison with other mitochondrial transport proteins." *Biochem J* 321(Pt 3): 713–9.

Issemann, I. and S. Green (1990). "Activation of a member of the steroid hormone receptor superfamily by peroxisome proliferators [see comments]." *Nature* 347(6294): 645–50.

Jeng, J. R., C. Y. Jeng, et al. (1997). "Gemfibrozil treatment of hypertriglyceridemia: improvement on fibrinolysis without change of insulin resistance." *Am Heart J* 134(3): 565–71.

Kallen, C. B. and M. A. Lazar (1996). "Antidiabetic thiazolidinediones inhibit leptin (ob) gene expression in 3T3–L1 adipocytes." *Proc Natl Acad Sci U S A* 93(12): 5793–6.

Keller, H., C. Dreyer, et al. (1993). "Fatty acids and retinoids control lipid metabolism through activation of perixisome proliferator–activated receptor–retinoid X receptor heterodimers." *Proc Natl Acad Sci U S A* 90(6): 2160–4.

Kemp, S. et al. (1998). Gene redundancy and pharmacological gene therapy: Implications for X–linked adrenoleukodystrophy. *Nature Medicine* 4(11):1261–1268.

Kliewer, S. A., K. Umesono, et al. (1992). "Convergence of 9–cis retinoic acid and peroxisome proliferator signalling pathways through heterodimer formation of their receptors." *Nature* 358(6389): 771–4.

Kliewer, S. A., B. M. Forman, et al. (1994). "Differential expression and activation of a family of murine peroxisome proliferator–activated receptors." *Proc Natl Acad Sci U S A* 91(15): 7355–9.

Kliewer. S. A., J. M. Lenhard, et al. (1995). "A prostaglandin J2 metabolite binds peroxisome proliferator–activated receptor gamma and promotes adipocyte differentiation." *Cell* 83(5): 813–9.

Kliewer. S. A., J. T. Moore, et al. (1998). "An orphan nuclear receptor activated by pregnanes defines a novel steroid signaling pathway." *Cell* 92(1): 73–82.

Knipscheer, H. C., J. C. de Valois, et al. (1996). "Ciprofibrate versus gemfibrozil in the treatment of primary hyperlipidaemia." *Atherosclerosis* 124 Suppl: S75–81.

Knopp, R. H. (1989). "Review of the effects of fenofibrate on lipoproteins, apoproteins, and bile saturation: US studies." *Cardiology* 76(Suppl 1): 14–22; discussion 29–32.

Kontopoulos, A.G., V. G. Athyros, et al. (1996). "Effects of simvastatin and ciprofibrate alone and in combination on lipid profile, plasma fibrinogen and low density lipoprotein particle structure and distribution in patients with familial combined hyperlipidaemia and coronary artery disease." *Coron Artery Dis* 7(11): 843–50.

Lemberger, T., B. Staels, et al. (1994). "Regulation of the peroxisome proliferator–activated receptor alpha gene by glucocorticoids." *J Biol Chem* 269(40): 24527–30.

Lock, E. A., A. M. Mitchell, et al. (1989). "Biochemical mechanisms of induction of hepatic peroxisome proliferation." *Annu Rev Pharmacol Toxicol* 29: 145–63.

Madsen, L., L. Froyland, et al. (1997). "Up–regulated delta 9–desaturase gene expression by hypolipidemic peroxisome–proliferating fatty acids results in increased oleic acid content in liver and VLDL: accumulation of a delta 9–desaturated metabolite of tetradecylthioacetic acid." *J Lipid Res* 38(3): 554–63.

Mangelsdorf, D. J., C. Thummel, et al. (1995). "The nuclear receptor superfamily: the second decade." *Cell* 83(6): 835–9.

Marcus, S. L., K. S. Miyata, et al. (1993). "Diverse peroxisome proliferator–activated receptors bind to the peroxisome proliferator–responsive elements of the rat hydratase/dehydrogenase and fatty acyl–CoA oxidase genes but differentially induce expression." *Proc Natl Acad Sci U S A* 90(12): 5723–7.

Martin, G., K. Schoonjans, et al. (1997). "Coordinate regulation of the expression of the fatty acid transport protein and acyl–CoA synthetase genes by PPARalpha and PPAR-gamma activators." *J Biol Chem* 272(45): 28210–7.

Mascaro, C., E. Acosta, et al. (1998). "Control of human muscle–type carnitine palmitoyltransferase I gene transcription by peroxisome proliferator–activated receptor." *J Biol Chem* 273(15): 8560–3.

Matsuura, K., A. Hara, et al. (1998). "Activation of human liver 3alpha–hydroxysteroid dehydrogenase by clofibrate derivatives." *J Pharmacol Exp Ther* 285(3): 1096–103.

Migdalis, I. N., B. Gerolimou, et al. (1997). "Effect of gemfibrozil on early carotoid atherscolerosis in diabetic patients with hyperlipidaemia." *Int Angiol* 16(4): 258–61.

Miller, C. W. and J. M. Ntambi (1996). "Peroxisome proliferators induce mouse liver stearoyl–CoA desaturase 1 gene expression." *Proc Natl Acad Sci U S A* 93(18): 9443–8.

Muerhoff, A. S., K. J. Griffin, et al. (1992). "The peroxisome proliferator–activated receptor mediates the induction of CYP4A6, a cytochrome P450 fatty acid omega–hydroxylase, by clofibric acid." *J Biol Chem* 267(27): 19051–3.

Nakagawa, S., Y. Kawashima, et al. (1994). "Regulation of hepatic level of fatty–acid–binding protein by hormones and clofibric acid in the rat." *Biochem J* 297(Pt 3): 581–4.

Osmundsen, H., J. Bremer, et al. (1991). "Metabolic aspects of peroxisomal beta–oxidation." *Biochim Biophys Acta* 1085(2): 141–58.

Paez Moreno, J. P. and G. Gonzalez (1989). "Comparative study of bezafibrate and probucol ion hyperlipidaemia." *Curr Med Res Opin* 11(8): 523–32.

Ricote, M., A. C. Li, et al. (1998). "The peroxisome proliferator–activated receptor–gamma is a negative regulator of macrophage activation." *Nature* 391(6662): 79–82.

Rodriguez, J. C., G. Gil–Gomez, et al. (1994). "Peroxisome proliferator–activated receptor mediates induction of the mitochondrial 3–hydroxy–3–methylglutaryl–CoA synthase gene by fatty acids." *J Biol Chem* 269(29): 18767–72.

Schafer, D., B. Hamm–Kunzelmann, et al. (1997). "Glucose regulates the promoter activity of aldolase A and pyruvate kinase M2 via dephosphorylation of Sp1." *FEBS Lett* 417(3): 325–8.

Soga, O., H. Kinoshita, et al. (1997). "Evaluation of peroxisomal heme in yeast." *J Biochem (Tokyo)* 121(1): 25–8.

Soltys, B. J. and R. S. Gupta (1996). "Immunoelectron microscopic localization of the 60–kDa heat shock chaperonin protein (Hsp60) in mammalian cells." *Exp Cell Res* 222(1): 16–27.

Staels, B., N. Vu–Dac, et al. (1995). "Fibrates downregulate apolipoprotein C–III expression independent of induction of peroxisomal acyl coenzyme A oxidase. A potential mechanism for the hypolipidemic action of fibrates." *J Clin Invest* 95(2): 705–12.

Staels, B., W. Koenig, et al. (1998). "Activation of human aortic smooth–muscle cells is inhibited by PPARalpha but not by PPARgamma activators." *Nature* 393(6687): 790–3.

Tomaszewski, K. E. and R. L. Melnick (1994). "In vitro evidence for involvement of CoA thioesters in peroxisome proliferation and hypolipidaemia." *Biochim Biophys Acta* 1220(2): 118–24.

Turpin, G. and E. Brucker (1996). "Efficacy and safety of ciprofibrate in hyperlipoproteinaemias." *Athersclerosis* 124 Suppl: S83–7.

Voskoboinik, I., R. Drew, et al. (1996). "Differential effect of peroxisome proliferators on rat glutathione S–transferase isoenzymes." *Toxicol Lett* 87(2–3): 147–55.

Vu–Dac, N., K. Schoonjans, et al. (1994). "Negative regulation of the human apolipoprotein A–I promoter by fibrates can be attenuated by the interaction of the peroxisome proliferator–activated receptor with its response element." *J. Biol Chem* 269(49): 31012–8.

Vu–Dac, N., K. Schoonjans, et al. (1995). "Fibrates increase human apolipoprotein A–II expression through activation of the peroxisome proliferator–activated receptor." *J Clin Invest* 96(2): 741–50.

Waldum, H. L., I. M. Kvetnoi, et al. (1998). "The effect of the peroxisome proliferator ciprofibrate on the gastric mucosa and particularly the gastrin cell." *J Mol Endocrinol* 20(1): 111–7.

Willumsen, N., J. Skorve, et al. (1993). "The hypotriglyceridemic effect of eicosapentaenoic acid in rats is reflected in increas ed mitochondrial fatty acid oxidation followed by diminished lipogenesis." *Lipids* 28(8): 683–90.

Winberg, L. D. and M. Z. Badr (1995). "Mechanism of phthalate–induced inhibition of hepatic mitochondrial beta–oxidation." *Toxicol Lett* 76(1): 63–9.

Woeltje, K. F., V. Esser, et al. (1990). "Cloning, sequencing, and expression of a cDNA encoding rat liver mitochondrial carnitine palmitoyltransferase II." *J Biol Chem* 265(18): 10720–5.

Yamazaki, N., Y. Shinohara, et al. (1995). "High expression of a novel carnitine palmitoyltransferase I like protein in rat brown adipose tissue and heart: isolation and characterization of its cDNA clone." *FEBS Lett* 363(1–2): 41–5.

Yang, F. Y., Y. G. Huang, et al. (1995). "Transmembrane Ca2+ gradient and function of membrane proteins." *Biosci Rep* 15(5): 351–64.

Yang, C. Y., Z. W. Gu, et al. (1996). "Effects of gemfibrozil on very–low–density lipoprotein composition and low–density lipoprotein size in patients with hypertriglyceridemia or combined hyperlipidemia." *Atherosclerosis* 126(1): 105–16.

Yoshida, H., T. Ishikawa, et al. (1998). "Beneficial effect of gemfibrozil on the chemical composition and oxidative susceptibility of low density lipoprotein: a randomized, double–blind, placebo–controlled study." *Atherosclerosis* 139(1): 179–87.

Zhu, Y., K. Alvares, et al. (1993). "Cloning of a new member of the peroxisome proliferator–activated receptor gene family from mouse liver." *J Biol Chem* 268(36): 26817–20.

Indiveri, C., V. Iacobazzi, et al. (1997). "The mitochondrial carnitine carrier protein: cDNA cloning, primary structure and comparison with the other mitochrondrial proteins." Pub Med nucleotide query.

* cited by examiner

| Gene Discovered | Accession Number | PPAR L vs. Vehicle control |
|---|---|---|
| PROTEIN PRODUCTION* | | |
|   PROTEIN FOLDING | | |
|     MOLECULAR CHAPERONE | | |
|       Heat shock protein 60 | X54793 | +3 |
| BASIC METABOLISM | | |
|   LIPID METABOLISM | | |
|     FATTY ACID SYNTHESIS | | |
|       Acetyl CoA carboxylase | J03808 | +2 |
|       Stearyl-CoA desaturase | J02585 | +5 |
|       Malic enzyme | M26581 | +7 |
|     FATTY ACID OXIDATION | | |
|       MITOCHONDRIAL BETA OXIDATION | | |
|         *Novel gene fragment, 299 bp, 92% S.I. to mouse carnitine acetyltransferase* | X85983 | NEW** |
|         Carnitine/acyl carnitine carrier protein | X97831 | +2 |
|         Delta-3-delta-2-enoyl CoA isomerase | M61112 | +15 |
|         Long chain acyl-CoA dehydrogenase | L11276 | +1.5 |
|         Medium chain acyl CoA dehdrogenase | J02791 | +6 |
|         Short chain acyl CoA dehdrogenase | J05030 | +2 |
|         Long chain enoyl-CoA hydratase/3-hydroxyacyl-CoA dehdrogenase | D16478 | +6 |
|         Long chain ketoacyl-CoA thiotase | D16479 | +4 |
|         Proplonyl-CoA thiotase | M14634 | +2 |
|       PEROXISOMAL BETA OXIDATION | | |
|         Very long chain acl-CoA synthetase | D85100 | +4 |
|         Carnitine octanoyl transferase | J02844 | +4 |
|         Acyl CoA odidase | J02753 | +6 |
|         *Novel gene fragment, 371 bp, 88% S.I. to rat acyl-CoA oxidase* | J02752 | +10 |
|         Enoyl-CoA hydrotase; 3-hydroxyacyl CoA bifunctional enzyme | K03249 | NEW |
|         Multifunctional enzyme type II | U37486 | +3 |
|       MICROSOMAL OMEGA OXIDATION | | |
|         Cytochrome p450 4A1 | X07259 | NEW |
|         Cytochrome p450 4A2 | M57719 | NEW |
|         Cytochrome p450 4A3 | M33936 | +3 |
|         Epoxide hydroiase | X65083 | +10 |
|     KETONE BODY METABOLISM | | |
|       Acetoacyetyl-CoA thioiase | D13921 | NEW |
|       3-hydroxy-3-methylgiutaryl CoA synthase | M33649 | +2 |
|   STEROID METABOLISM | | |
|     BILE ACID SYNTHESIS | | |
|       Steroid-3V dehydrogenase | D17310 | OFF*** |
|     EXCRETION | | |
|       Hydroxysteroid sulfotransferase | M31363 | -6 |
|       Cytochrome p450 M1 | J02657 | -3 |
|       Androgen repressible liver protein SMP-2 | J02643 | -5 |
|       UDP-glucosuronyl transferase-21 | M33747 | -6 |
|   CARBOHYDRATE METABOLISM | | |

Fig. 1A

| Gene Discovered | Accession number | PPAR L vs. Vehicle control |
|---|---|---|
| *Novel gene fragment, 467 bp, 90% S.I. to human UDP-glucose pyrophosphorylasse* | U27460 | -8 |
| AMINO ACID METABOLISM | | |
| Histidina decarboxylase | M29591 | +6 |
| BIOSYNTHESIS OF COFACTORS, PROSTHETIC GROUPS, CARRIERS | | |
| HEME & PORPHYRIN | | |
| *-aminoievulinate synthase | J04044 | +4 |
| Porphobilinogen deaminase | X06827 | NEW |
| DETOXIFICATION | | |
| Cytochrome p450, phenobarbital inducible [CYP2B1] | J00719 | +1.5 |
| Catalase | M16670 | +12 |
| Metallothionein-1 | J00750 | OFF |
| Glutathione transferase Ya sumit | X00520 | -3 |
| METABOLITE STORAGE/TRANSPORT PROTEINS | | |
| EXTRACELLULAR STORAGE | | |
| Apolipoprotein A-1 | X00588 | -2 |
| INTROCELLULAT STORAGE | | |
| Liver fatty acid binding protein | J00732 | +2.5 |
| Acyl-CoA hydroiase | D88891 | +4 |
| Acyl-CoA thioesterase | U49694 | +5 |
| TISSUE ARCHITECTURE | | |
| CYTOSKELETON | | |
| Dymein-like protein 3 | D26494 | NEW |
| UNKNOWN FUNCTION | | |
| NOVEL GENES/GENE FRAGMENTS | | |
| *Novel gene fragment, 420 bp* | | +4 |
| *Novel gene fragment, 284 bp* | | +3 |
| *Novel gene fragment, 145 bp* | | *NEW* |
| *Novel gene fragment, 173 bp* | | *NEW* |
| *Novel gene fragment, 234 bp* | | *+12* |
| *Novel gene fragment, 279 bp* | | *+6* |
| *Novel gene fragment, 124 bp* | | *NEW* |
| *Novel gene fragment, 360 bp* | | *NEW* |
| REPETITIVE ELEMENTS | | |
| SATELLITE DNA | | |
| Satellite DNA (isolated by Sau3ai digest) | J00784 | *NEW* |
| * Cellular functional foles assigned upon primary role the gene displays | | |
| ** New indicates de novo expression of designated gene in the treated with no detectable expression in the controls. | | |
| *** Off indicate complete lack of expression in the treated rates for a gene detected in the control rates. | | |

| Gene Discovered | Acc# | Confirmed Bands | PPARα treated vs. vehicle control (2821) | Dictionary Definitions |
|---|---|---|---|---|
| BASIC METABOLISM | | | | |
| 4.1.: LIPID METABOLISM | | | | |
| 4.1.2.: FATTY ACID OXIDATION | | | | |
| 4.1.2.1.: MITOCHONDRIAL BETA OXIDATION | | | | |
| Novel gene fragment, 299 bp, 92% S.I. to mouse carnitine acetyltransferase (X85983) | | m0v0_298.5 | NEW | The enzyme that transfers C2-C6 acyl groups fro CoA to carnitine for import into both the mitochondria and peroxisomes. |
| Carnitine/acyl carnitine carrier protein | X97831 | m0v0_359.4 | +2 | The enzyme that shuttles acyl carnitines in and carnitines out of the mitochondria |
| Delta-3-delta-2-enoyl CoA isomerase | M61112 | l0h0_63.8, l0u0_223.8 | +15 | The enzyme that, in unsaturated fatty acid oxidation in mitochondria, moves the double bond from a delta-3 to a delta-2 position to make the bond accessible to the fatty acid oxidation machinery. |
| Long chain acyl-CoA dehydrogenase | L11276 | l0m0_91.7 | +15 | Plays a crucial role in the dehydrogenation of C8-C18 fatty acids, the first step in mitochondrial beta oxidation. Defects in this prevent the utilization of the major fatty acids,C16 & C18, for energy. (OMIM #201460) |
| Medium chain acyl-CoA dehydrogenase | J02791 | l0h0_148.7 | +6 | Covers the initial dehydrogenation of C4-C12 straight chain acyl-CoA's in mitochondrial beta oxidation |
| Short chain acyl CoA dehydrogenase | J05030 | l0l0_59.4 | +2 | Covers the initial dehydrogenation of C2-C4 straight chain acyl-CoA's. As butyrates are most commonly found in the muscles, defects in this enzyme can lead to myopathies (OMIM #201470). |
| Long chain enoyl-CoA hydratase/3-hydroxyacyl-CoA dehydrogenase | D16478 | g1l0_284.2, m1n0_384.7 | +6 | Mitochondrial bifunctional enzyme is the second and third steps of fatty acid beta oxidation. The enzyme takes the newly unsaturated product from the dehydrogenase, adds an H2O to consume the double bond making a 3-hydroxyl group. The Second part of the h |
| Long chain ketoacyl-CoA thiolase | D16479 | g0m0_105.1, m0r0_221.8 | +4 | Final step in mitochondrial beta oxidation. Uses CoA-SH to cleave the 3-ketoacyl-CoA freeing up acetyl-CoA to go into the krebs cycle and adding a new CoA group onto the now-exposed 3-keto group to create an acyl-CoA n-2 shorter than the previous acyl-CoA |
| Propionyl-CoA carboxylase | M14634 | h0r0_239.2 | +2 | Enzyme has a dual function. In odd chained fatty acid beta oxidation, the last product is the 3-carbon propionyl-CoA. This enzyme adds HCO3- to propionyl-CoA to create d-methylmalonyl-CoA which is then isomerized to the l-isoform by vitamin B12. The l-iso |

| Gene Discovered | Acc# | Confirmed Bands | PPARα treated vs. vehicle control (2821) | Dictionary Definitions |
|---|---|---|---|---|
| 4.1.2.2.: PEROXISOMAL BETA OXIDATION | | | | |
| Very long chain acyl-CoA synthetase | D85100 | h0a0_241.8, m0v0_431.8 | +4 | Peroxisomal enzyme whose activity is lacking the the X-linked disorder adrenoleukodystrophy. People with the disease have an unusually high abundance of 24-30 carbon fatty acid in brain & adrenal membranes. Defect in disease is in the catabolism of the ve |
| Carnitine octanoyl transferase | J02844 | l0h0_162.9 | +4 | Enzyme in peroxisomal beta oxidation. Interconverts the middle chain fattyacids found outside the mithochondria into carnitine-carriers to facilitate their importation into the peroxisomes for peroxisomal beta oxidation. |
| Acyl CoA oxidize | J02752 | l0u0_133.7, d0g0_301.1 | +6 | First step in peroxisomal beta-oxidation. Have activity for acyl-CoA carbon chains between C4 and C16. Catalyzes their conversion to alpha-beta enoyl-CoA (induction of double bonds) products with concomitant reduction of the buffer-dissolved O2 to H2O2. P |
| Novel gene fragment, 371 bp, 88% S.I. to rat acyl-CoA oxidase [J02752] | | m0v0_382 | ±10 | First step in peroxisomal beta-oxidation. Have activity for acyl-CoA carbon chains between C4 and C16. Catalyzes their conversion to alpha-beta enoyl-CoA (induction of double bonds) products with concomitant reduction of the buffer-dissolved O2 to H2O2. P |
| Enoyl-CoA hydratase: 3-hydroxyacyl CoA bifunctional enzyme | K03249 | r0s0_275.5, m0n0_286.2, r0s0_222.1, s0g1_120.4 | NEW/ | Involved in peroxisomal fatty acid oxidation. Catalyses the hydration of straight-chain (2E)-enoyl-CoAs to (3S)-hydroxyacyl-CoAs and then dehydrogenation to 3-ketoacyl-CoA. |
| Multifunctional enzyme type II | U37486 | r0s0_361.6 | +3 | Involved in fatty acid oxidation. Catalyses the hydration of straight-chain (2E)-enoyl-CoAs to (3R)-hydroxyacyl-CoAs, but it is devoid of hydratase 1[(2E)-enoyl-CoA to (3S)-hydroxyacyl-CoA: what the bifunctional enzyme does] and (3R)-hydroxyacyl-CoA dehy |
| Acyl-CoA hydrolase | D88891 | l0a0_271.2 | +4 | Catalyzes the hydrolysis of CoA from palmitoyl and longer chain fatty acids. Liver isoform induced by peroxisome proliferators. Exact function unknown. Significantly expressed in liver after peroxisome proliferato treatment. |
| Acyl-CoA thioesterase | U49694 | l0a0_409 | +5 | Homologous to but distinct from the liver acyl-CoA hydrolase. Incomplete lipase activity-cleaves CoA from palmitoyl. Precise role has yet to be determined. |

Fig. 2B

| Gene Discovered | Acc# | Confirmed Bands | PPARα treated vs. vehicle control (2821) | Dictionary Definitions |
|---|---|---|---|---|
| 4.1.2.3.: MICROSOMAL OMEGA OXIDATION | | | | |
| Cytochrome p450 4A1 | X07259 | w0h0_420.2 | NEW | AKA: cytochrome P450 4A1, p452. Involved in lauric acid (C12) omega hydroxylation. Induced in rodents by peroxisome proliferators through PPAR-alpha. Posttranslationally suppressed by interferon, IL-1beta, IL-6. |
| Cytochrome p450 4A2 | M57719 | i0r0_338.3, r0s0_309.1 | NEW | Microsomal enzyme. The entire class of CYP4A enzymes catalyze the formation of 20-hydroxyeicosatetraenoic acids (20-Hete's: potent effects on renal vasculature and tubular iron transport) via omega hydroxylation, and |
| Cytochrome p450 4A3 | M33936 | r0s0_317.9, s0g1_371.9 | +3 | 11,12 epoxidation of arachidonic acid. Also induced with clofibrate. Lauric acid omega hydroxylase. |
| Epoxide hydrolase | X65083 | i0a0_333.0, i0s0_238.1, h0a0_288.7 | +10 | The enzyme responsible for the immediate metabolism of cis-epoxyeicosatrienoic acids (EETs), methyl cis-epoxyeicosatrienoates, and cis epoxyeicosanoic acids with the creation of diols where the epoxide residue used to be. Works in balance with CYP2C8 whi |
| 4.1.1.: FATTY ACID SYNTHESIS | | | | |
| Acetyl CoA carboxylase | J03808 | d0g0_46.8 | +2 | First committed step in fatty acid biosynthesis. Takes acetyl-CoA + HCO3- and forms malonyl-CoA. Uses biotin as a cofactor. Fatty acid synthesis then proceeds by adding acetyl-CoA to the malonyl-CoA to make acetoacetyl-CoA and release $CO_2$. (Stryer p.614). |
| Stearyl-CoA desaturase | J02585 | h0a0_176.5, i00_52.1, s0g1_88.3, m1s0_107.3, i0a0_42.2, g1l0_85.2, f0h0_359.5, s0h0_203.2 | +5 | Part of the microsomal system for introduction of double bonds into saturated fatty acid chains. Stearyl-CoA desaturase takes the C18 stearate and adds a cis-delta-9 double bond to create oleyl-CoA. |
| Malic enzyme | M26581, M26594, M26585 | l0n0_182.3, d0v0_82.2, i0n0_202.1, m0r0_190.0, m0v0_283.6 | +7 | Enzyme in fatty acid sythesis that cycles malate to produce NADPH from NADP+. The NADPH is then used as the reducing agent and a source of hydrogens for chain elongation in fatty acid synthase. |

Fig. 2C

| Gene Discovered | Acc# | Confirmed Bands | PPARα treated vs. vehicle control (2821) | Dictionary Definitions |
|---|---|---|---|---|
| 4.1.3.: KETONE BODY METABOLISM | | | | |
| Acetoacetyl-CoA thiolase | D13921 | m0r0_338.3, d0g0_419.0, m1s0_391.5 | NEW | First step in ketone body synthesis. Two molecules of acetyl-CoA condense to form acetoacetyl-CoA and release CoASH. |
| 3-hydroxy-3-methylglutaryl CoA synthase | M33649 | b1l0_128.2 | +2 | Second step in ketone body metabolism. Acetoacetyl-CoA is reacted with acetyl-CoA and H2O to give HMG-CoA and CoASH. The HMG-CoA can also be shunted to cholesterol biosynthesis but if ketone bodies are needed, then HMG-CoA is cleaved into acetyl-CoA and a |
| 4.2.3.: BILE ACID SYNTHESIS | | | | |
| Steroid-3α dehydrogenase | D17310 | i0m0_240.0 | OFF | Enzyme plays a multifunctional role in metabolizing steroid hormones, polycyclic aromatic hydrocarbons, and prostaglandins and also in transforming the steroid nucleus for the biosynthesis of bile acids from cholesterol in liver. Catalyzes the first step |

| Gene Discovered | Acc# | Confirmed Bands | PPARα treated vs. vehicle control (2821) | Dictionary Definitions |
|---|---|---|---|---|
| 4.2.4.: EXCRETION | | | | |
| Hydroxysteroid sulfotransferase | M31363 | g0m0_96.1 | -6 | Catalyzes the conversion of hydroxylated steroids to their sulfated moiety which is the principal pathway for steroid excretion. These can include the androgen based DHEA, pregnenalone and glucocorticoids. There are 3 isoforms of hepatic hydroxysteroid s |
| Cytochrome p450 M1 | J02657 | d0g0_223.6 | -3 | AKA rat CYP2C11. Cytochrome with male-specific expression in rat livers. Most abundant cytochrome in untreated male rat livers. Know for metabolizing testosterone mainly in positions 2 alpha and 16 alpha. Also hydroxylates C-21 of progesterone. This place |
| Androgen repressible liver protein SMP-2 | J02643 | g0m0_200.2 | -5 | AKA: isoform of hydroxysteroid sulfotransferase. Functions in excretion of steroid hormones. Specific subrates of this isoform unknown. Constitutive liver protein. The steady state level is repressed by androgen so that in male rats, the lowest levels a |
| UDP-glucosuronyl transferase-21 | M33747 | g1i0_208.5, i0m0_206.6 | -6 | AKA: UPGTr-5. Member of the steroid UDP- glucuronosyl-transferases. Expressed enzyme glucuronidates testosterone and dihydrotestosterone, although its activity towards these two substrates is about 30-fold less than that of UDPGTr-3. UDPGTr-5 is another 17 |
| 4.3.: CARBOHYDRATE METABOLISM | | | | |
| 4.3.2.: GLYCOGEN MANIPULATION | | | | |
| Novel gene fragment, 467 bp, 90% S.I. to human UDP-glucose pyrophosphorylase [U27460] | | i0n0_235.7 | -8 | Enzyme that catalyzes the formation of UDP-glucose. UDP-glucose is the method by which glucose moieties are added to nascent glycogen chains. It adds UMP to Glucose-1-P with the hydrolysis of Ppi. UDP-glucose is then added to glycogen by glocogen synthas |

| Gene Discovered | Acc# | Confirmed Bands | PPARα treated vs. vehicle control (2821) | Dictionary Definitions |
|---|---|---|---|---|
| 4.7.: BIOSYNTHESIS OF COFACTORS, PROSTHETIC GROUPS, CARRIERS | | | | |
| 4.7.3.: HEME & PORPHYRIN | | | | |
| δ-aminolevulinate synthase | J04044 | a1s0_189.2 | +4 | First & rate limiting step in porphyrin and heme biosynthesis. Involves the condensation of glycine and succinyl-CoA to form delta-aminolevulinate. |
| Porphobilinogen deaminase | X06827 | s0w0_40.6 | NEW | In the heme biosynthesis pathway, two delta-aminolevulinates condense to form porphobilinogen. Then 4 porphobilinogens are condensed head to tail to form a linear tetrapyrrole. This is catalyzed by porphobilinogen deaminase. An ammonium ion is released to |
| 4.5.: AMINO ACID METABOLISM | | | | |
| 4.5.6.: HISTIDINE FAMILY | | | | |
| Histidine decarboxylase | M29591 | h0a0_178.5 | +6 | Enzyme responsible for the conversion of histidine to histamine. Histamine is a CNS neurotransmitter and a stimulus for the release of gastric acid. Histidine decarboxylase is expressed in the liver and selected brain regions. |
| 4.9.: DETOXIFICATION | | | | |
| 4.9.1.: MONOOXYGENASES | | | | |
| Cytochrome p450, phenobarbital inducible [CYP2B1] | J00719 | l0a0_61.6, l0s0_198.4 | +15 | Member of the CYP2B family (CYP2B1, CYP2B2, CYP2B3). Phenobarbital induces these enzymes via a c-AMP dependant PKA cascade. Class of cytochromes particularly involved in metabolism of xenobiotics-7,12,dimethylbenza-anthracine. Monooxygenases. This subset |

Fig. 2F

| Gene Discovered | Acc# | Confirmed Bands | PPARα treated vs. vehicle control (2821) | Dictionary Definitions |
|---|---|---|---|---|
| 4.9.2.: OXYGEN RADICALS | | | | |
| Catalase | M16670 | m0v0_91.3 | +12 | Ubiquitous heme protein that scavenges hydrogen peroxides to convert them to water and molecular oxygen. Reaction= 2 H2O2 = 2 H2O + O2. |
| 4.9.3.: HEAVY METALS | | | | |
| Metallothionein-1 | J00750 | i0l0_239.7 | OFF | Metallothioneins are cysteine-rich metal binding proteins typically inducible by metal ions, also inducible by glucocorticoids. Substrates include cadmium and zinc. Induction occurs with increase in heavy metal concentrations- metallothioein functions to |
| 4.9.5.: HYDROCARBONS | | | | |
| Glutathione transferase Ya subunit | X00520 | m1s0_230.7 | -3 | One of the members of the glutathione-S-transferase isoenzymes. One subunit of the alpha isoform. Part of the battery of aryl hydrocarbon-activated genes in the liver. One of the activators of this system is dioxin. Transcription is regulated by the Ah-me |
| 4.11.: METABOLITE STORAGE/TRANSPORT PROTEINS | | | | |
| 4.11.1.: EXTRACELLULAR TRANSPORT | | | | |
| 4.11.1.2.: LIPIDS | | | | |
| Apolipoprotein A-1 | X00558 | r0s0_332.0, m0r0_367.0 | -2 | Alias: prostacyclin Stabilizing factor. Major protein of HDL and a relatively abundant plasma protein with concentration of 1.0 mg/ml. Major cofactor for lecithin:cholesterol acyltransferase which is responsible for the formation of most cholesteryl ester |

Fig. 2G

| Gene Discovered | Acc# | Confirmed Bands | PPARα treated vs. vehicle control (2821) | Dictionary Definitions |
|---|---|---|---|---|
| 4.11.3.: INTERACELLULAR STORAGE <br> 4.11.3.1.: LIPIDS | | | | |
| Liver fatty acid binding protein | J00732 | m0r0_260.0 | +2.5 | Abundant constituent of the cytoplasm that regulates lipid metabolism and transport. It binds free fatty acids, their CoA derivatives, bilirubin, organic anions, and other small molecules. Liver fatty acid-binding protein is required for cholesterol synth |
| 5.: TISSUE ARCHITECTURE <br> 5.1.: CYTOSKELETON <br> 5.1.1.: COMPONENT <br> 5.1.1.1.: MOTOR ARM | | | | |
| Dynein-like protein 3 | D26494 | r0s0_119.1 | NEW/ | Protein isloated from rat brain cDNA library using degenerate primers from dynein catalytic domain consensuses. Putative assignment to motor/propellant function asociated with all dyneins. |
| 1.: PROTEIN PRODUCTION <br> 1.3.: PROTEIN FOLDING <br> 1.3.1.: MOLECULAR CHAPERONE | | | | |
| Heat shock protein 60 | X54793 | a1s0_138.8 | +3 | Stress-induced heat shock protein. Molecular chaperone involved in protein folding. Along with hsp10, specially transported to the mitochondria to regulate protein folding within that organelle. Overexpression of hsp60/hsp 10 has been shown to be protectiv |

Fig. 2H

| Gene Discovered | Acc# | Confirmed Bands | PPARα treated vs. vehicle control (2821) | Dictionary Definitions |
|---|---|---|---|---|
| 9.: UNKNOWN FUNCTION | | | | |
| 9.4.: NOVEL GENES/GENE FRAGMENTS | | | | |
| Novel gene fragment, 420 bp | AA964752 | m0r0_161.2 | +4 | |
| Novel gene fragment, 284 bp | | f0i0_107.7, s0h0_181.7 | +3 | |
| Novel gene fragment, 145 bp | | b1i0_145.0 | NEW | |
| Novel gene fragment, 173 bp | | g0m0_173.1 | NEW | |
| Novel gene fragment, 234 bp | | g1n0_234.3 | +12 | |
| Novel gene fragment, 279 bp | | y0i0_279.2 | +6 | |
| Novel gene fragment, 124 bp | | l0a0_123.9 | NEW | |
| Novel gene fragment, 360 bp | H35859 | m0v0_283.6 | NEW | |
| REPETITIVE ELEMENTS | | | | |
| SATELLITE DNA | | | | |
| Satellite I DNA (isolated by Sau3ai digest) | J00784 | r0s0_43.2 | NEW | |

Fig. 21

Gene Discovered

4.: BASIC METABOLISM
4.1.: LIPID METABOLISM
4.1.1.: FATTY ACID SYNTHESIS

| Gene Discovered | Acc# | Confirmed Bands | PPARα treated vs. vehicle control (2821) | Dictionary Definitions |
|---|---|---|---|---|
| Malic enzyme | M26581, M30596, M26594, M26585 | d0y0_182.8, d0y0_82.6, g1l0_192.5, i0s0_159.6, u0g1_276.6, m0v0_283.7, l0n0_182.3 | +100 | Enzyme in fatty acid synthesis that cycles malate to produce NADPH from NADP+. The NADPH is then used as the reducing agent and a source of hydrogens for chain elongation in fatty acid synthase. |
| Tricarboxylate transport protein | L12016 | m0v0_217.6 | +4 | Protein in fatty acid synthesis that transports citrate synthesized in the mitochondria from oxaloacetate an acetyl-CoA across the mitochondrial membrane to the cytosol where the citrate is reconverted to oxaloacetate and acetyl-CoA. The acetyl-CoA is su |
| ATP-citrate lyase | J05210 | I0h0_71.2, i0a0_111.3 | +90 | Enzyme in fatty acid synthesis that takes cytosolic citrate and cleaves off acetyl CoA to enter the fatty acid synthesis cycle. |
| Fatty acid synthase | M76767 | n0s0_405.1 | +40 | Enzyme in fatty acid synthesis that takes malonyl-CoA + acetyl-CoA and used the energy of NADPH to form Cn + 2 fatty acid backbones. System is good up to C16. |
| Stearyl-CoA desaturase | J02585 | h0a0_176.9, i0a0_142.1, m1s0_102.5, g1l0_84.1 | +20 | Part of the microsomal system for introduction of double bonds into saturated fatty acid chains. Stearyl-CoA desaturase takes the C18 stearate and adds a cis-delta-9 double bond to create oleyl-CoA. |

4.1.2.: FATTY ACID OXIDATION
4.1.2.1.: MITOCHONDRIAL BETA OXIDATION

| Gene Discovered | Acc# | Confirmed Bands | PPARα treated vs. vehicle control (2821) | Dictionary Definitions |
|---|---|---|---|---|
| Carnitine/acyl carnitine carrier protein | X97831 | m1n0_94.0 | -1.5 | The enzyme that shuttles acyl carnitines in and carnitines out of the mitochondria |
| Long chain 3-ketoacyl thiolase | D16479 | d0g0_85.2 | +1.5 | Final step in mitochondrial beta oxidation. Uses CoA-SH to cleave the 3-ketoacyl-CoA freeing up acetyl-CoA to go into the krebs cycle and adding a new CoA group onto the now-exposed 3-keto group to create an acyl-CoA n-2 shorter than the previous acyl-CoA |

Fig. 2J

| Gene Discovered | Acc# | Confirmed Bands | PPARα treated vs. vehicle control (2821) | Dictionary Definitions |
|---|---|---|---|---|
| 4.1.4.: PHOSPHOLIPID BIOSYNTHESIS | | | | |
| Novel gene fragment, 744 bp, 83% S.I. to mouse glycerol-3-phosphate acyltransferase [M77003] | | g1n0_273.6 | +20 | Enzyme is the first committed step towards the formation of glycerophospholipids. Takes glycerol-3-phosphate and adds an acyl group to C1 (saturated chain) or C2 (unsaturated chain). Two isoforms: mitochondrial and microsomal. Mitochondrial isoform prefer |
| 4.1.6.: EICOSANOID METABOLISM | | | | |
| 4.1.6.5.: HETE PATHWAYS | | | | |
| 12-lipoxygenase | L06040 | l0u0_153.6 | -5 | Introduces a molecular oxygen in arachidonic acid in the C-12 position to create 12(S)-hydroperoxy-5,8,10,14-eicosatetraenoic acid (12-S HETE). The major pathway of arachidonic acid metabolism in human platelets proceeds via a 12-lipoxygenase enzyme. |
| 4.3.: CARBOHYDRATE METABOLISM | | | | |
| 4.3.1.: GLYCOLYSIS/GLUCONEOGENESIS | | | | |
| Phosphoenolpyruvate carboxykinase | K03243 | l0r0_202.8 | +2 | The glycolytic enzyme pyruvate kinase which converts phosphoenolpyruvate to pyruvate is not reversible in gluconeogenesis. Two enzymes are needed to reverse the glycolytic step. The first, pyruvate carboxylase, takes pyruvate + CO2 +ATP to make oxaloacet |
| 4.3.2.: GLYCOGEN MANIPULATION | | | | |
| Glycogen synthase | J05446 | s0g1_129.1 | +100 | New glucosyl units are added to the nonreducing terminal residues of glycogen. Glycogen synthase transfers the activated glycosyl unit from UDP-glucose to the hydroxyl group at the C4 terminus of glycogen to form an alpha-1,4-glycosidic linkage. The UDP i |

Fig. 2K

| Gene Discovered | Acc# | Confirmed Bands | PPARα treated vs. vehicle control (2821) | Dictionary Definitions |
|---|---|---|---|---|
| 4.9.: DETOXIFICATION | | | | |
| 4.9.2.: OXYGEN RADICALS | | | | |
| Catalase | M16670 | m0v0_91.4 | +8 | Ubiquitous heme protein that scavenges hydrogen peroxides to convert them to water and molecular oxygen. Reaction= $2 H_2O_2 \to 2 H_2O + O_2$. |
| 4.8.: CENTRAL INTERMEDIARY METABOLISM | | | | |
| 4.8.2.: SULFUR METABOLISM | | | | |
| Rhodanese | X56228 | m0r0_374.4 | -2 | EC 2.8.1.1. Nuclear-encoded mitochondrial thiosulfate sulfotransferase. involved in forming iron-sulfur compounds and cyanide detoxification and modification of sulfur containing enzymes. Converts cyanide to thiocyanate. |
| 4.4.: OXIDATIVE PHOSPHORYLATION | | | | |
| 4.4.1.: CITRIC ACID CYCLE | | | | |
| Novel gene fragment, 434 bp, 91% S.I. to human nuclear aconitase [U80040] | | r0v0_213.6 | +2 | Nuclear encoded aconitase found in mitochondria. Has an iron-sulfur group in its center. Step in citric acid cycle that converts citrate to isocitrate through an aconitate intermediate. |
| 4.4.2.: ELECTRON TRANSPORT CHAIN | | | | |
| NADH-ubiquinone oxidoreductase chain 4 | C06662 | i0s0_180.8 | +80 | One of seven mitochondrially encoded residues (out of 40 total) for the first step of the electron transport chain. (UI#92389317) |
| Cytochrome C oxidase polypeptide I | S79304 | f0i0_293.9 | +100 | Encoded in the mitochondrial genome. One of 3 cytochrome C oxidase subunits encoded in the mitochondrial genome. Subunits 4-8 are nuclear encoded. Cytochrome C oxidase is the last step in the electron transport chain and is responsible for collecting elec |

| Gene Discovered | Acc# | Confirmed Bands | PPARα treated vs. vehicle control (2821) | Dictionary Definitions |
|---|---|---|---|---|
| 4.4.3.: ATP/PROTON MOTIVE FORCE INTERCONVERSION | | | | |
| Adenine nucleotide translocator | D12771 | d0g0_158.6 | +2 | Alias: adenine nucleotide translocator 1. Most abundant mitochondrial protein. Exsist as a homodimer of two 30 kDa subunits. The dimer forms a gated pore that shuttles ADP across the mitochondrial membrane. ANT determines the rate of ADP/ATP flux between |
| Uncoupling protein-2 | AB010743 | m0v0_382, g0m0_120, I0m0_162, m0v0_137 | +1.5 | Uncoupling protein-2 has 59% amino acid identity to UCP1, the primary regulator for thermogenesis in brown adipose tissue. UCP-2, however, is expressed in all tissues, including tissue rich in macrophages, and it is upregulated in white fat in response t |
| 4.2.: STEROID METABOLISM | | | | |
| 4.2.3.: BILE SALT BIOSYNTHESIS | | | | |
| Δ4-3-ketosteroid 5β reductase | D17309 | a1s0_117.9 | -50 | Catalyzes the reduction of delta-4-3-oxosteroids to give the cis conformation, This is a key enzyme in bile acid synthesis as in some infants with liver disease, 3-oxo-delta 4 bile acids are the major bile acids in urine, a phenomenon attributed to reduce |
| 4.11.: INTRACELLULAR METABOLITE STORAGE/TRANSPORT PROTEINS | | | | |
| 4.11.1.: EXTRACELLULAR TRANSPORT | | | | |
| 4.11.1.1.: OXYGEN | | | | |
| Major α globin | M17803 | g0s0_231 | -10 | One of the two protein constituents of adult major hemoglobin, fetal hemoglobin and A2 hemoglobin. Hemoglobin forms a tetramer of two alpha-class chains and two beta-class chains and serves as the major carrier of molecular oxygen in the blood to peripher |
| β globin | X05080 | m1s0_199.7 | -7 | Beta globin form the beta-class component of adult major hemoglobin, where two beta chains heterodimerize with two alpha chains (alpha-1 chains for major hemoglobin A2 chains for minor hemoglobin). Hemoglobin serves as the major carrier of molecular oxyge |

| Gene Discovered | Acc# | Confirmed Bands | PPARα L treated vs. vehicle control (2821) | Dictionary Definitions |
|---|---|---|---|---|
| 4.11.2.: PLASMA MEMBRANE SHUTTLING | | | | |
| Fatty acid transport protein | U89529 | s0h0_97, i0s0_170 | +1.5 | Membrane transporter for long chain fatty acids. Northern blots showed high levels of FATP in 3T3-L1 adipocytes with a major 2.9-kb transcript and a minor 3.8-kb form. Expression increased 5-fold during differentiation of preadipocytes to adipocytes. In n |
| 4.11.3.: INTRACELLULAR STORAGE | | | | |
| 4.11.3.1.: LIPIDS | | | | |
| Adipocyte fatty acid binding protein | U75581 | l0h0_144.7 | +5 | Marker for differentiated adipocyte cells. Binds to carboxylate ends of fatty acids. Comprises 1% of all cytosolic protein in adipose tissue. Lack of protein causes obesity on a high-fat diet. However, despite the obesity, no development of insulin resist |
| 5.: TISSUE ARCHITECTURE | | | | |
| 5.1.: CYTOSKELETON | | | | |
| 5.1.1.: COMPONENTS | | | | |
| 5.1.2.: STRUCTURAL ARM-INTERMEDIATE FILAMENTS | | | | |
| Keratin 19 | X81449 | h0a0_218.1 | -15 | Keratin proteins belong to 2 families: acidic (or type I) and basic (or type II). As a rule they are coordinately synthesized in pairs so that at least 1 member of each family is expressed in each epithelial cell. The most striking exception to the kerati |
| 5.1.3.: REGULATORS | | | | |
| 5.1.3.2.: INHIBITORS | | | | |
| Brain S-100β subunit | X01090 | f0f0_286.2 | +90 | Most abundantly expressed in glial cells but found to be expressed in many tissues. Maps to human chromosome 21 and may be a candidate for dysregulation in Down's Syndrome. Two calcium binding domains. May be involved in the signalling to cause axonal gro |

| Gene Discovered | Acc# | Confirmed Bands | PPARα treated vs. vehicle control (2821) | Dictionary Definitions |
|---|---|---|---|---|
| 5.2.: EXTRACELLULAR MATRIX | | | | |
| 5.2.1.: COMPONENT | | | | |
| Novel gene fragment, 181 bp, 93% S.I. to mouse fibrillin [u22493] | | i0i0_180.7 | +70 | Single stranded glycoprotein found in the extracellular matrix of elastic tissues. Gene associated with marfan's syndrome. |
| 5.2.3.: BREAKDOWN INHIBITION | | | | |
| SPI-3 serine protease inhibitor | X16359 | s0h0_155.5, u0g1_318.1 | -5 | Liver acidic glycoprotein that is barely present in normal rats is induced by inflammation. TRanscriptional regulation by IL-6 and glucocorticoids. Promoter is activated by STAT 3 & 5B. Up to 90% amino acid identity with SPI-1 & SPI-2 except in region of |
| WAP four disulfide core domain protein [ps20] | AF037272 | u0g1_194.4 | +1.5 | Gene initially isolated from a urogenital sinusmesenchymal cell line and shown to have growth-inhibitory properties. Member of the class of WAP serine protease inhibitors. Exerts growth inhibition in a wide range of cell types. Unsure if this is related t |
| 2.: SIGNAL TRANSDUCTION | | | | |
| 2.2.: PEPTIDE HORMONES/GROWTH FACTORS/CYTOKINES | | | | |
| 2.1.2.: GROWTH FACTORS | | | | |
| Novel gene fragment, 63 bp, 92% S.I. to mouse nov gene [X97863] | | l0n0_62.7 | -100 | Cysteine rich protein overexpressed in avian nephroblastomas. Shares sequence homology with CCN proteins that include the IGFBP's and connective tissue growth factor. Involved in growth regulation. Secreted protein. |
| 2.2.: PEPTIDE RECEPTORS | | | | |
| 2.2.2.: G-PROTEIN COUPLED RECEPTORS | | | | |
| β3 adrenergic receptor | M74716 | w0i0_97.1 | +2 | G-protein coupled seven transmembrane receptor, activation stimulates Gs. Definitvely involved in thermoregulation and in lipolysis:evolutionarily is linked to brown fat and its use for uncoupled Ox-Phos to generate heat in hibernating animals. Evidence |

| Gene Discovered | Acc# | Confirmed Bands | PPARα1 treated vs. vehicle control (2821) | Dictionary Definitions |
|---|---|---|---|---|
| 2.2.3.: TRANSMEMBRANE 4 SUPERFAMILY | | | | |
| Novel gene fragment, 317 bp, 100% identity to overlapping residues of human transmembrane 4 superfamily protien SAS [Q12999] | | I0h0_316.9 | -1.0 | AKA=SAS. Protein found to be amplified in sarcomas including liposarcoma. Transmembrane 4 superfamily proteins are transmembrane receptor proteins involved in regulation of growth processes. Other members of family include VEGF-R, GCSF-R and some integrin |
| 2.4.: G-PROTEINS | | | | |
| 2.4.1.: ALPHA SUBUNITS | | | | |
| GTP binding protein (Gα-i2) | M17528 | u0g1_78.5 | -1.5 | Originally cloned out of olfactory epithelium. Subunit of G-proteins. The alpha subunit tends to be the effector subunit. When no ligand is bound to the associated receptor, the alpha subunit stays bound to the beta/gamma complex and is complexed with GD |
| 2.14.: DNA BINDING PROTEINS | | | | |
| 2.14.1.: TRANSCRIPTION FACTORS | | | | |
| Novel gene fragment, 106bp, 83% S.I. to mouse relB [M83380] | | I0h0_109.2 | ±1.0 | Transcription factor of the NFkB class and can heterodimerize with NFkB. Binding to NFkB is shown to regulate chemokine expression which modulates local inflammation. Also essential for proper dendritic cell differentiation. Mutant mice lack antigen prese |

Fig. 2P

| Gene Discovered | Acc# | Confirmed Bands | PPARα treated vs. vehicle control (2821) | Dictionary Definitions |
|---|---|---|---|---|
| 3.: CELL CYCLE | | | | |
| 3.6.: CELL DEATH REGULATION | | | | |
| 3.6.2.: APOPTOSIS INHIBITION | | | | |
| Novel gene fragment, 258, bp 97% S.I. To mouse BAP31 [X81816] | | l0h0_259.2 | +10 | Member of a highly conserved family of integral membrane proteins found to be binding proteins of immunoglobulins. ER protein that seems to be involved in the earliest trafficking of integral endosome membrane proteins to the earliest endosomes-like cellu |
| 6.: EXTRACELLULAR ENVIROMENTAL REGULATION | | | | |
| 6.2.: IMMUNE SYSTEM | | | | |
| 6.2.1.: COMPLEMENT | | | | |
| 6.2.1.1.: COMPONENTS | | | | |
| Novel gene fragment, 531 bp, 86% S.I. to human complement component C1r [M14058] | | r0s0_105.2 | -30 | Component of the classical complement pathway. One of three proteins to make up the C1 unit. Two molecules each of the smaller C1r & C1s bind to a unit of C1q. The binding of C1q to a single bound IgM molecule leads to the enzymatic activation of C1r. The |
| 6.2.2.: CELL SURFACE SIGNALLING | | | | |
| 6.2.2.1.: MHC PROTEINS | | | | |
| Novel gene fragment, 316 bp, 63% amino acid identity to intracytoplasmic region of rat MHC class II B-1β [P29826] | | l0h0_316.9 | -7 | Beta light chain for the MHC class II alpha/beta heterodimer. MHC class II molecules are responsible for antigen presentation for proteins in the extracellular matrix compartment. |

Fig. 2Q

| Gene Discovered | Acc# | Confirmed Bands | PPARα treated vs. vehicle control (2821) | Dictionary Definitions |
|---|---|---|---|---|
| 8.: INTRACELLULAR TRAFFIC | | | | |
| 8.1.: VESICLES | | | | |
| 8.1.2.: COATAMER COMPONENTS | | | | |
| Novel gene fragment, 713 bp, 83% S.I. to cow coat protein γ-cop [X70019] | | s0y0_42.7 | -5 | Gamma-COP is one protein subunit of coatemer coats from non-clathrin containing vesicles. These are the vesicles that mediate constitutive secretory transport in cells. Gamma-COP is mammalian component of yeast Sec21. |
| 9.: UNKNOWN FUNCTION | | | | |
| 9.1.: KNOWN GENES | | | | |
| 9.1.2.: UNASSOCIATED | | | | |
| Insulin-induced growth response protein (CL-6) | L13619 | g1n0_293.0 | +30 | Alias: insulin-introduced-gene-1 (INSIG1). Gene was discovered following treating liver cells with insulin-a growth stimulatory agent and then collecting differentially expressed proteins. CL-6 is the most abundantly induced insulin-responsive gene in their |
| 9.4.: NOVEL | | | | |
| Novel gene fragment, 407 bp | | w0i0_425.7 | +35 | |
| Novel gene fragment, 120 bp | | d0y0_120.1 | -100 | |
| Novel gene fragment, 231bp | | s0y0_42.7 | -100 | |
| Novel gene fragment, 315 bp | | u0g1_318.1 | +1.0 | |
| Novel gene fragment, 178 bp | | u0g1_178.1 | -20 | |

Fig. 2R

| Gene Discovered | Acc# | Confirmed Bands | PPARα treated vs. vehicle control (2821) | Dictionary Definitions |
|---|---|---|---|---|
| 4.: BASIC METABOLISM | | | | |
| 4.1.: LIPID METABOLISM | | | | |
| 4.1.1.: FATTY ACID SYNTHESIS | | | | |
| Tricarboxylate transport protein | L12016 | u0a0_193.5(O) | +9 | Protein in fatty acid synthesis that transports citrate synthesized in the mitochondria from oxaloacetate and acetyl-CoA across the mitochondrial membrane to the cytosol where the citrate is reconverted to oxaloacetate and acetyl-CoA. The acetyl-CoA is su |
| 4.1.2.: FATTY ACID OXIDATION | | | | |
| 4.1.2.3.: MICROSOMAL OMEGA OXIDATION | | | | |
| Cytochrome P450 IVA2 | M57119 | g0s0_62.0(T&O), i0n0_337.9(O), m0s0_218.2(O), r0s0_319.0(O), g0m0_275.0(Q) | +6 | Microsomal enzyme. The entire class of CYP4A enzymes catalyze the formation of 20-hydroxyeicosatetraenoic acids (20-HETE's: potent effects on renal vasculature and tubular iron transport) via omega hydroxylation, and 11,12 epoxidation of arachidonic acid |
| Cytochrome p450 IVA3 | M33936 | s0g1_264.5(T&O), m0s0_261.0(T) | +5 | Also induced with clofibrate. Lauric acid omega hydroxylase. |
| 4.1.4.: PHOSPHOLIPID BIOSYNTHESIS | | | | |
| Novel gene fragment, 744bp, 83% SI to mouse glycerol-3-phosphate acyltransferase [M77003] | | g1n0_273.6(T), i0n0_273.8(T) | -2 | Enzyme is the first committed step towards the formation of glycerophospholipids. Takes glycerol-3-phosphate and adds an acyl group to C1 (saturated chain) or C2 (unsaturated chain). Two isoforms: mitochondrial and microsomal. Mitochondrial isoform prefer |
| 4.3.: CARBOHYDRATE METABOLISM | | | | |
| 4.3.1.: GLYCOLYSIS/GLUCONEOGENESIS | | | | |
| Glyceraldehyde-3-phosphate dehydrogenase | M17701 | f0k0_125.7(O) | +10 | Enzyme in glycolysis that catalyzes the conversion of glyceraldehyde-3-phosphate to 1,3-bisphosphoglycerate. |

Fig. 2S

| Gene Discovered | Acc# | Confirmed Bands | PPARα treated vs. vehicle control (2821) | Dictionary Definitions |
|---|---|---|---|---|
| 4.3.3.: OLIGO/POLYSACCHARIDES | | | | |
| 4.3.3.1.: ASSEMBLY | | | | |
| UDP-glucose dehydrogenase | AB013732 | m1e1_67.1(O) | +3 | Enzyme that converts UDP-glucose to UDP-glucuronate, a critical component of the glycosaminoglycans, hyaluronan, chondroitin sulfate, and heparan sulfate. (UI# 98411308) |
| 4.4.: OXIDATIVE PHOSPHORYLATION | | | | |
| 4.4.1.: CITRIC ACID CYCLE | | | | |
| Succinyl-CoA synthetase alpha subunit | J03621 | w0i0_78.1(T) | -3 | Enzyme in the citric acid cycle that catalyzes the conversion of succinyl-CoA to succinate and yields GTP. Only step in citric acid cycle that yields a high energy bond. |
| 4.4.2.: ELECTRON TRANSPORT CHAIN | | | | |
| Cytochrome C oxidase polypeptide I-mitochondrial | S79304 | f0k0_169.9(O) | +40 | Encoded in the mitochondrial genome. One of 3 cytochrome C oxidase subunits encoded in the mitochondrial genome. Subunits 4-8 are nuclear encoded. Cytochrome C oxidase is the last step in the electron transport chain and is responsible for collecting elec |
| Novel gene fragment, 695 bp, 83% SI and 92% amino acid identity to cow B22 subunit of the NADH-ubiquinone oxidoreductase complex [X64836] | | r0s0_252.9(O) | -2 | One of 40 subunits for NADH-ubiquinone oxidoreductase, the first step of the oxidative phosphorylation electron transport chain. Seven of the polypeptides are mitochondrially encoded and the rest are nuclear transcripts that are imported into the mitochon |

Fig. 2T

| Gene Discovered | Acc# | Confirmed Bands | PPARα treated vs. vehicle control (2821) | Dictionary Definitions |
|---|---|---|---|---|
| 4.2.: STEROID METABOLISM | | | | |
| 4.2.4.: EXCRETION | | | | |
| UDP-glucosuronosyl transferase | Y00156 | i0r0_122.0(T) | +1.5 | 17-B hydroxysteroid glucuronosyltransferase for degradation. |
| 4.5.: AMINO ACID METABOLISM | | | | |
| 4.5.4.: PYRUVATE FAMILY | | | | |
| Alanine aminotransferase | D10354 | g0l0_196.7(O) | -2 | Catalyzes the aminotransfer of the alanine NH2 group to α-ketoglutarate. This yields pyruvate, which is fed into the glycolytic pathway and glutamate. |
| 4.5.1.: AROMATIC AMINO ACID FAMILY | | | | |
| Tyrosine aminotransferase | M18340 | i0s0_291.5(T) | -2 | Enzyme is regulated by glucocorticoids and retinoic acid. Hepatocyte-specific marker of glucocorticoid activity. Catalyzes the addition of NH2 group to hydroxyphenylpyruvate to form tyrosine. However, this enzyme has been used as a marker in many studies |
| 4.8.: CENTRAL INTERMEDIARY METABOLISM | | | | |
| 4.8.3.: CATECHOLAMINE METABOLISM | | | | |
| Catechol-O-methyltransferase | M60754 | i0s0_185.1(T), f0l0_74.4(O) | +4 | Degrades norepinephrine and epinephrine. Liver has high level of production of this enzyme and any circulating epi or norepi gets filtered when passing through hepatic circulation. |

Fig. 2U

| Gene Discovered | Acc# | Confirmed Bands | PPARα treated vs. vehicle control (2821) | Dictionary Definitions |
|---|---|---|---|---|
| 4.11.: METABOLITE STORAGE/TRANSPORT PROTEINS | | | | |
| 4.11.1.: EXTRACELLULAR TRANSPORT | | | | |
| 4.11.1.3.: STEROIDS | | | | |
| Vitamin D binding protein | J05148 | u0a0_195.1(O) | +15 | Alias: Gc globulins. Member of multigene family that includes alpha-fetoprotein and albumin. Major carrier of vitamin D and its metabolites in the blood. High expression levels in the liver. Potent inhibitor of nanomolar range Ca+2 sensing by osteoclasts. |
| 4.11.1.4.: HYDROCARBONS | | | | |
| Submaxillary gland alpha-2-mu globulin | J00738 | l0m0_311.7(T) | +25 | Also synthesized in the liver. Expression in the liver is correlated with androgenization of the male rat. Serum fraction binds hydrocarbons and filters these for excretion in the kidney-this function may be related to the nephrotoxicity of these compound |
| 2.: SIGNAL TRANSDUCTION | | | | |
| 2.11.: KINASES | | | | |
| 2.11.4.: KINASE INHIBITORS | | | | |
| Novel gene fragment, 156 bp, 92% SI to mouse protein kinase inhibitor gamma [U97170] | | w0l0_155.6(T) | +5 | Protein kinase inhibitor with 35% identity to PKIalpha and 30% identity to PKIbeta1. Residues important for the high affinity of PKIalpha and PKIbeta 1 as well as nuclear export of the catalytic (C) subunit of cAMP-dependent protein kinase were found to be |

Fig. 2V

| Gene Discovered | Acc.# | Confirmed Bands | PPARα treated vs. vehicle control (2821) | Dictionary Definitions |
|---|---|---|---|---|
| 2.13.: CALCIUM CASCADE | | | | |
| 2.13.2.: PHOSPHOLIPASE C ISOFORMS | | | | |
| Phospholipase C-1 | M20636 | l0s0_291.5(T) | -2 | Cleaves phosphatidyl inositol into diacylglycerol and 1,4,5 inositol triphosphate. PLC tends to be activated by G-proteins of subtype Go. |
| 2.14.: DNA BINDING PROTEINS | | | | |
| 2.14.1.: TRANSCRIPTION FACTORS | | | | |
| *Novel gene fragment, 1084 bp, 100% amino acid identity to rat hepatocarcinogenesis- related transcription factor [JC4875]* | | h0r0_278.6(O) | +2 | Basic leucine zipper protein initially found as overexpressed in rat hepatocellular carcinomas. HTF had a considerable homology with human XBP/TREB5, which has been reported to be a binding factor for the X-box of the MHC class II gene and for the 21-bp e |
| 1.: PROTEIN PRODUCTION | | | | |
| 1.2.: mRNA TRANSLATION | | | | |
| 1.2.1.: RIBOSOMAL PROTEINS | | | | |
| Ribosomal protein L18 | M20156 | g0s0_129.6(T) | -2 | Binds 5S rRNA. Found to be overexpressed in human colon cancer. |
| 1.3.: PROTEIN FOLDING | | | | |
| 1.3.2.: DISULFIDE BOND REGULATION | | | | |
| *Novel gene fragment, 514 bp, 83% SI to human protein disulfide isomerase related protein [D49490]* | | s0l1_93.6(O) | +2 | ER resident protein. Has a motif for oxidoreductase activity. Preferentially expressed in cells actively secreting proteins and is shown to be stress induced. These results suggested that PDIR has oxidoreductase activity of disulfide bonds against polypep |

Fig. 2W

| Gene Discovered | Acc# | Confirmed Bands | PPARα treated vs. vehicle control (2821) | Dictionary Definitions |
|---|---|---|---|---|
| 5.: TISSUE ARCHITECTURE <br> 5.2.: EXTRACELLULAR MATRIX <br> 5.2.2.: BREAKDOWN | | | | |
| Novel gene fragment, 165 bp, 67% SI to human cathepsin O [X77383] | | f0h0_164.6(O) | +2.5 | Novel cathepsin derived from cultured monocyte-derived macrophages. Endopeptidase which cleaves fibrinogen at an acid pH. Highly similar to rat osteoclast-derived protease. |
| 6.: EXTRACELLULAR ENVIRONMENTAL REGULATION <br> 6.2.: IMMUNE SYSTEM <br> 6.2.1.: COMPLEMENT <br> 6.2.1.1.: COMPONENTS | | | | |
| Novel gene fragment, 136 bp, 83% SI to human complement protein C8 beta subunit [M16973] | | i0m0_79.1(O) | +1.5 | Member of the lysis pore component of the final step of the complement cascade. Has distinct gene locus and mRNA sequence from C8 alpha subunit despite high sequence homology. C8 beta has highest similarity to C9 alpha subunit indicating probable genetic |
| 6.2.1.2.: INHIBITORY REGULATION | | | | |
| Novel gene fragment, 789 bp, 88% SI to mouse complement factor I (C3b/C4b inactivator) [U47810] | | m0a0_288.4(O) | +3 | Proteolytic enzyme that destroys the hemolytic and immune-adherence activities of cell-bound activated C3. Factor I is composed of 2 disulfide-linked polypeptide chains with molecular weight of 50,000 and 38,000 daltons. It is synthesized as a single-chai |
| 7.: CELLULAR ORGANELLE STRUCTURAL INTEGRITY <br> 7.2.: ENDOPLASMIC RETICULUM/GOLGI APPARATUS <br> 7.2.2.: TRANSMEMBRANE PROTEINS | | | | |
| Endoplasmic reticulum transmembrane protein | Y07783 | r0k0_363.7(O) | +3 | Alias: Differentially expressed in rat intestine (Dri 42). |

Fig. 2X

| Gene Discovered | Acc# | Confirmed Bands | PPARα treated vs. vehicle control (2821) | Dictionary Definitions |
|---|---|---|---|---|
| 9.: UNKNOWN FUNCTION | | | | |
| 9.1.: KNOWN GENES | | | | |
| 9.1.2.: UNASSOCIATED | | | | |
| Novel gene fragment, 141 bp, 89% SI to human KIAA0315 [AB002313] | | h0c0_97.3(O) | +6 | BLAST nucleotide search yields almost perfect homology to: human MM1 product (cDNA differentially expressed in brain tumors). |
| 9.1.: PUTATIVE HOMOLOGIES | | | | |
| Novel gene fragment, 270 bp, 64% amino acid similarity to rat HES-1 (hairy and enhancer of split) transcription factor [Q04666] | | p0t0_214.8(O) | +1 | |
| 9.4.: NOVEL GENE FRAGMENTS | | | | |
| Novel gene fragment, 189 bp | | w0i0_188.8(T) | +2 | |
| Novel gene fragment, 584 bp | | l0n0_89.7(T) | -100 | |
| Novel gene fragment, 45 bp | | r0a0_46.3(O) | -1.5 | |
| Novel gene fragment, 63 bp | | m0a0_77.5(O) | +5 | |
| Novel gene fragment, 96 bp | | h0c0_97.3(O) | +20 | |
| Novel gene fragment, 315 bp | | s0y0_114.2(O) | +2 | |
| Novel gene fragment, 169 bp | | f0k0_169.9(O) | +10 | |
| Novel gene fragment, 391 bp | | m0a0_135.1(O) | +2 | |
| Novel gene fragment, 45 bp | | y0k0_44.9(O) | -2 | |

Fig. 2Y

| Gene Discovered | Acc# | Confirmed Bands | PPARα treated vs. vehicle control (2821) | Dictionary Definitions |
|---|---|---|---|---|
| REPETETIVE DNA ELEMENTS | | | | |
| LINE'S | | | | |
| L1 retrotransposon m1vi2-m38 [Found in CYP4A2 5' region 2x] | U87604 | h0r0_120.3(T) | -15 | |
| L1 retrotransposon, ORF 2 [Found in CYP2A2] | X61295 | n0s0_112.9(O) | -10 | |
| L1 RnB7 repetitive DNA element [Found in CYP4A2 5' region 2x] | X07687 | i0c0_86.4(O) | -5 | |
| L1 retrotransponson m1vi2-m8 [Found in CYP4A2 5' region] | U87598 | h0r0_123.3(T) | -8 | |
| LINE DNA cotaining 7 ORF's | X53581 | m0n0_97.0(O), p0h1_364.5(O) | -6 | |
| Long interspersed repetive DNA element LINE3 | | r0s0_188.0(T), m0r0_117.8(T), w0i0_70.1(T), h0r0_83.7(T), i0a0_83.0(T), g1l0_267.4(O) | -2 | |
| *Novel LINE element, 326 bp,* [Found in CYP2C13] | M13100 | w0i0_55.6(T) | -100 | |
| OTHER REPETITIVE ELEMENTS | | | | |
| 2.4 kb repeat DNA left terminal region | X50473 | r0s0_135.9(T) | -100 | |
| satellite I core DNA | M30113 | r0s0_134.0(T) | -20 | |

Fig. 2Z

|  |  | PPARαL treated vs.vehicle control | |
|---|---|---|---|
| Gene | Accession Number | Data obtained by GeneCalling™ | Data obtained by RT-PCR |
| Acyl CoA oxidase | J02752 | +6 | +5 |
| Enoyl-CoA hydrotase: 3-hydroxyacyl CoA bifunctional enzyme | K03249 | *de novo* | +35 |
| Cytochrome P450 4A1[1] | X07259 | *de novo* | +45 |
| Stearyl-CoA desaturase | J02585 | +5 | +6 |
| Malic enzyme | M26594 | +7 | +7 |
| Hydroxysteroid sulfotransferase | M31363 | -6 | -3 |

[1] The enzymatic activity of Cytochrome P450 4A1 (lauric acid ω-hydroxylase) increased 28-fold following PPARαL treatment

Fig. 3

Fragment 1: f0h0_291.2(Fragment 3:f0i0_107.7)

```
  1 cctaggcatt tagcatccat ntactagagt ttaaagtntc ctgtgggttc ataaataata
 61 gggaaggtat tttgatttaa tttanacagt tgatgcnant ganannctna agnntttnnc
121 nattanttta cacatagcnc gtggtanttg ggnnnattna ccnaatgnct tagancnttg
181 gnnaacacna ntantcangn ncacaaangt gtagnngnaa tttnantgna aacatnnatn
241 acnaaacnat gnttcnggng nttaccccaa tnnc
```

Fragment 2: b1io_145

```
  1 rccggtgcgt agtcttgggt gaaatgttaa ntatgcactg atcctcagga agttgggttc
 61 gaaagggaga taaattacca aagtggtcca agaattgtat atgtggagaa acccatgtta
121 gagaaagaaa tcatatactc agatct
```

Fragment 3: g0m0_173.1

```
  1 TCATGAGGCCNATTCGCTCCACTGTGGCCCGCAGCCCCCGGAATTCATCAGTNAGCGCCTTATTCTTGGTGGGTTCAAAG
 81 CTGGGCTGCTCCGGAGCTAGCTCTCCAATCAGAAGAGAGTTCATATACTTTCTCACAAGGCCCTTGTTAATGTGGAATGC
161 CACAAAAGGATCCGTGGCATCCTGACCAGCGTAGTGGCTGATGNACCGGGAGCCTCCCGGGTGGTCCGCGACTGAAGTCG
241 CTGATGTTGTACA
```

Fragment 4: g1n0_234.3

```
  1 tgtacagtta agtggaaatg agaactctgc actaagtaac tgctttccgt gaatgtgaag
 61 aagattcttg caaagtggac tcaggacctt ggcactgtat ttgtaaaatg ataatgtgct
121 ttgagaaaac cttaggggga gggggatga aagaaattaa agtggtaaaa caagacaaat
181 atgagtaaat gcctattttt actgtaacat taattatgtc taataaattt ctaga
```

Fragment 5: y0i0_279.2

```
  1 agatctttac tgagaagaaa tggctgctct ctaactggga gtagtgaaaa gtccaagggc
 61 atctactttc tactcttaaa aagatgtgca ttttatattt taattagatc ctctacactc
121 taacattaac atatctgttc aaacttgtct agttgccaag tggctgaga gtgttaagat
181 ttaaatcctt tttggagtat ctctgagagt agtctggaag caaaatgttc tcctctcagg
241 atgatgtcat ttgtgaagca gggaaacatg gagaactagt
```

Fragment 6: 10a0_123.9

```
  1 ggtaccagga agctgtggaa aaggtgctgt taagatcatt ccccaatcag gtcttcagag
 61 tccctgtgac cgacgcacag aacttcagct tctggcggtc caacagccca ggcgtgcgtc
121 cgga
```

Fig. 4A

Fragment 7 : Rat EST H35859(m0v0_283.6)

```
  1 tcatgatgat agcctcctcc tccaggttct cccgaagaat ctgcagggtc ctgcggtcct
 61 tctctgcctg gaggagtggc atgagggcga tcctggcctc caagtcctcg atcagcaggc
121 gcctacgctc ccggttccac ctcattattc tccagtagcc aaagatcaag gccccgatgc
181 ccaaagcaaa catgctgtat cccgacagtc cccggcggac aggtttccgc ttgtagtcga
241 tggggccgta gcccctggtg gggaattgtc ctgcttcacc t
```

Fragment 8 : Rm0v0_382.0(homologous to rat acyl-coA oxidase mRNA)

```
  1 catgaacccc gacctgcgca aggagcgggc ctccgccacc ttcaatccgg agttgatcac
 61 gcacatcttg gatggcagtc cggagaatac ccggcgccgt cgagaaattg agaacttgat
121 tctgaacgac ccagacttcc agcatgagga ctataacttc ctcactcgaa gaccagcgtt
181 atgaggtggc tgttaagaag agtgccacca tggtgaagaa gatgagggaa tatggcatct
241 cggaccctga agaaatcatg tggtttaaaa actctgtgca ccgncggcat cctgagcctt
301 tggaccttca cttgggcatg ttcctaccca ccttgcttnc cngnccancg gagagnngca
361 ggagngcttc ttcatgccgg c
```

Additionnal information for Fragment 8
BLASTIN: Identities = 323/364 (88%), Positives = 323/364 (88%)
gb:GENBANK-ID:RATACOA1lacc:J02752 Rat acyl-coA oxidase mRNA, complete cds-Rattus norvegicus, 3741 bp (RNA). Length=3741

Blast-X: Identities = 56/56 (100%), POSITIVES = 56/56 (100%), ptnr:SWISSPROT-ACC: P07872 ACYLCOENZYME A OXIDASE, PEROXISOMAL (EC 1.3.3.6)(PALMITOYL-COA OXIDASE)(AOX)- RATTUS NORVEGICUS (RAT), 661 aa.

Fragment 9:m0v0_298.5(homolog to mouse mRNA for carnitine acetyltransferase)

```
  1 gccggccaga tgcttcatgg tggtggcagc aagttcaaca gtggcaaccg ctggttcgac
 61 aagacactgc agtttattgt ggcagaagat ggctcctgtg ggatggttta tgaacatgca
121 gctgcagaag ggccccccat tgtcgctctt gtggaccatg tcatggagta tacaaagaag
181 cctgaacttg tgcggtcccc tatggtaccc ctgcctatgc ccaagaagct gcggttcaac
241 atcacacctg agatcaagaa tgacatagag aaggccaaac agaacatcag catcatga
```

Additionnal information for Fragment 9
Blast-N: Identities = 277/298 (92%), Positives = 277/298 (92%),
gb:GENBANK-ID:MMRNACARlacc:X85983 M.musculus mRNA for carnitine acetyltransferase - Mus musculus, 2596 bp (RNA)

Fig. 4B

Fragment 10: m0r0_161.2

```
  1 AGTTTTGTAAACAGCTAATTTTATTCCTTGATACCAATTGGTTGTTCATGATACATACTTTTCTGCAAGAAGGCAATGAA
 81 TGAAATAAAGGCATAGAGGGGAAATTGGGGAAAAACCACAATGTAGTAGGATGTCACTTAATTAAACTCGTACTTGATTG
161 GCTAGTTGTTTTAGTTACAATTTCAAGTCTTATAGATACAGAATTCTACTTTTTTTCCAGAACAAACATATATGTCCTTA
241 AAGACAGTGGGGGAGACAACAGATTTTTAACTGCTGAGCTTCTTACTTCTAAGGAGAACAGTCAACATTGTTACTTCTTG
321 TCCTTCACAGTCTGGAATTCATGTGGGTCATTAGCTTCTCCAATTTGATTGCTANGGCTATGTTTCCTTTAATCTTCAAC
401 TTTCCTGACATAAATGCCAT
```

Fragment 11: 10n0_235.7 (homolog to human uridine diphosphoglucose pyrophosphorylase mRNA)

```
  1 AAAGCTATGNTCTCAAGATGGGGGCTTCTCAGTTCCAAGAGGGTCATTCTCCAAGAACTAGAATTATCTGTGAAGAAAGA
 81 ATTAGAAAAAATACTTACCACAGCAACCTCACATGAGTTTGAGCACACTAAGAAAGATCTTGNATGGATTTCGGAAGCTA
161 TTTCACAGATTTTTGCAAGAAAAGGGGCCTTCTGTAGACTGGGGTAAAATCCAGAGACTCCGGAAGATTCGATTCAACCC
241 TATGAAAAGATAAAGGCCAGAGGCTTGCCTGATAACATATCTTCTGTGTTGAACAAACTGGTGGTAGTGAAACTCAATGG
321 TGGTTTGGGAACCAGCATGGGCTGCAAAGGCCCTAAAAGTCTGATTGGTGTAAGAAATGAGAATACCTTTTTGGATCTAA
401 CCGTTCAGCAAATTGAACATCTGAACAAAACCTATAATACAGATGTCCCGCTCGTATTAATGAATTC
```

Additional information for Fragment 11
Blast-N: Identities = 424/467 (90%) Positives = 424/467 (90%),
gb:GENBANK-ID:HSU27460|acc:U27460 Human uridine diphosphoglucose pyrophosphorylase mRNA, complete cds - Homo sapiens, 1823 bp (RNA). Length = 1823

Blast-X: Identities = 121/155 (78%) Positives = 127/155 (81%),
ptnr:SWISSPROT-ACC:Q07131 UTP--GLUCOSE-1-PHOSPHATE URIDYLYLTRANSFERASE (EC2.7.7.9) (UDP-GLUCOSE PYROPHOSPHORYLASE)(UDPGP) - HOMO SAPIENS (HUMAN), 507aa.

Fig. 4C

COMPOSITIONS AND METHODS RELATING TO THE PEROXISOMAL PROLIFERATOR ACTIVATED RECEPTOR-α MEDIATED PATHWAY

RELATED APPLICATIONS

This application claims priority to U.S. Ser. No. 60/108,293, filed Nov. 13, 1998, and No. 60/126,465, filed Mar. 26, 1999, each of which are incorporated herein by reference in their entirety.

FIELD OF THE INVENTION

The invention relates generally to the identification of agents for treating pathophysiologies associated with peroxisomal proliferator activated receptor-α (PPARα), and of identifying ligands for PPARα, and of identifying agents for treating these pathophysiologies. More particularly, the invention relates to methods of diagnosing these pathophysiologies, and of identifying agents for treating these pathophysiologies, using nucleic acids whose expression changes following addition to cells of a ligand for PPARα.

BACKGROUND OF THE INVENTION

Elevated low-density lipoprotein (LDL) cholesterol has long been recognized as an independent risk factor for the development of coronary artery disease and subsequent myocardial ischemia and infarction. There is also growing evidence that elevated triglycerides may also present a significant independent risk factor for development of coronary heart disease.

Increased triglyceride-rich lipoprotein remnants play a central role in increased atherosclerosis in several dyslipoproteinemias. Elevated triglycerides associated with low HDL is a frequent genetic dyslipoproteinemia in patients with established cardiovascular disease.

The fibrate class of lipid lowering agents have been demonstrated effective in managing coronary artery disease. Fibrates include the marketed drugs clofibrate (Atromid), Gemfibrozil (Lopid), Fenofibrate (Lipidil), ciprofibrate (Lipanor) and the experimental compound bezafibrate, These fibrates have been characterized as peroxisome proliferators based upon their ability to increase peroxisome number and activity in rodent model systems. Molecular characterization of the peroxisome proliferator activated receptor α (PPARα), and subsequent pharmacological analysis of the fibrate compounds has demonstrated that these compounds are ligands of the PPARα. PPARα is expressed in the liver, kidney and heart. Natural ligands for the receptor include C16–C20 polyunsaturated monocarboxylic fatty acids (PUFA).

The lipid lowering effects of fibrates are directly mediated through PPARα. These receptors are members of the nuclear receptor superfamily of ligand-dependent transcription factors. Three subtypes of mammalian PPAR's have been characterized: -alpha, -gamma, -delta. Members of the PPAR family exert their effect on transcriptional regulation through heterodimerization of ligand-bound PPAR receptors with the retinoid X receptor (RXR). These activated receptors bind to PPAR response elements (PPRE's) in DNA to initiate a transcriptional response.

Peroxisomes, a class of subecclular organelles with which PPARα is associated, are enclosed by a single-layered membrane. Currently, more than 50 metabolically relevant enzymatic activities have been characterized within the peroxisome. These include β-oxidation of long-chain fatty acids and derivatives (dicarboxylic acids, prostanoids, some xenobiotics and the side chain of cholesterol), fatty acid elongation, the hydrolysis of acyl-CoA's and their conversion to acylcarnitines, biosynthesis of ether glycerolipids, cholesterol and dolichols, the catabolism of purines, polyamines and amino acids and the metabolism of reactive oxygen species. Various in vivo and in vitro drug-dosing models have each associated one or two genes from these pathways with PPARα ligand activity. However, a comprehensive analysis of PPARα ligand-mediated activity has not been described.

SUMMARY OF THE INVENTION

The present invention is based in part on the discovery of changes in expression patterns of multiple nucleic acid sequences in rodent liver cells following exposure to a ligand for a PPARα. The nucleic acid sequences whose expression changes include nucleic acid sequences encoding previously described polypeptides, as well as heretofore undescribed nucleic acid sequences. Expression of a subset of the sequences increased in liver cells following addition of the PPARα ligand, while expression of other sequences decreased following exposure to the ligand.

Based in part on the identification of these PPARα ligand responsive nucleic acid sequences, the invention provides screening methods based on nucleic acid sequences responsive to PPARα ligands. Also provided are methods for diagnosing or assessing conditions associated with PPARα metabolism using genes differentially expressed in response to PPARα ligands, as well as methods of treating adrenoleukodystrophy using PPARα ligands. In other aspects, the invention provides nucleic acid collections for identifying agents and pathologies associated with PPARα ligand responsive nucleic acid sequences. The invention additionally provides substrate arrays for identifying agents and pathologies associated with PPARα ligand responsive nucleic acid sequences, as well as single nucleotide polymorphisms associated with PPARα ligand responsive genes. The PPARα-mediated disorders described herein can include, e.g, the pathophysiology is selected from the group consisting of: adrenoleukodystrophy; hyperlipidemia; peroxisomal disorders; dyslipidemia; hypertriglyceridemia; coronary artery disease; myocardial ischemia and infarction; and disorders associated with lipid metabolism, fatty acid metabolism, ketogenesis, microsomal-oxidation, and fatty acid-oxidation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE FIGURES

FIGS. 1A and 1B depict a list of genes described previously as responsive to PPARα ligand.

FIGS. 2A–2Z depict a list of polypeptides encoded by nucleic acid sequences newly shown to be PPARα ligand responsive in liver. Column 1 discloses the names of the genes discovered and their GenBank Accession Number ("Acc#"), if known. Column 2 discloses the name of the band confirmed by GENECALLING® ("confirmed bands"). Column 3 discloses the level of PPARα ligand upregulation compared to the control ("PPARαL treated vs. vehicle control (2821)"). Column 4 provides more detailed information about the disclosed protein encoded by the PPARαL upregulated gene ("dictionary definitions").

FIG. 3 depicts a comparison of the level of upregulated RNA expression of six genes when analyzed by GENECALLING®™ versus RT-PCR. Column 1 provides the name of the gene discovered ("gene"), while Column 2 provides its GenBank Accession Number ("Acc #"). Columns 3 and 4 compare data obtained by GENECALLING®™ (Quantitative Expression Analysis, "QEA") with data obtained by quantitative RT-PCR ("RT-PCR").

FIGS. 4A–4C depict the sequences [SEQ ID NOS:1–11] of novel gene fragments described herein.

DETAILED DESCRIPTION OF THE INVENTION

The present invention is based in part on the discovery of changes in expression patterns of multiple nucleic acid sequences, including sequences encoding known genes as well as heretofore undescribed nucleic acid sequences, in rodent liver cells following exposure to a ligand for a PPARα. The differences in gene expression were identified following administration of 1.5 mg/kg/day of a PPARα-specific ligand named GW9578. This compound is described in Brown et al., J. Med. Chem.42:3785–8, 1999, whose contents are incorporated herein in their entirety.

GW9578 was administered to male 10–14 week old Sprague Dawley rats in b.i.d. dosing for 3 days. The animals were sacrificed 24 hours following the last dose, and liver tissue was analysis using the GENECALLING® sequence identification methods described U.S. Pat. No. 5,871,697. The contents of this application are incorporated herein by reference in their entirety.

The GENECALLING® sequence identification method is performed by digesting a cDNA with a pair of restriction endonucleases. The digested fragments are differentially tagged at both the 3- and 5'-termini, and amplified via polymerase chain reaction (PCR) with a fluorescent label that is detected upon subsequent electrophoresis. In the studies with PPARα ligand GW9578, a total of 48 different reactions were performed, each with a unique pair of restriction enzymes. Analysis of gel electrophoresis chromatograms demonstrated that 8973 different gene fragments were expressed in liver. This number represents a non-redundant coverage of approximately 85% of the total number of hepatic genes.

The hepatic response to treatment with the PPARαL compound was determined by comparing in triplicate the relative abundance of each of the 8973 gene fragments in the PPARαL-treated vs. the PPARα-untreated rodents. Comparison was performed using commercially available GENESCAPE® expression analysis software. PPARαL administration detectably altered the expression of 218 of the 8973 (2.4%) hepatic genes fragments by greater than 1.5-fold. The identity of each of these differentially-expressed genes was determined by finding the gene possessing a matching restriction fragment length within a rat gene sequence database using GENESCAPE® expression analysis software. Novel genes, corresponding to fragments with no match within the database, were subsequently isolated and sequenced (FIG. 4). Independent confirmation of differences in gene expression was obtained for a total of 84 gene fragments, including all 51 gene fragments which were demonstrated to be modulated by more than 5-fold (See FIG. 2). There was an excellent correlation between the expression analysis results derived by the GENECALLING® sequence identification methods in comparison with those results previously obtained by the use of reverse transcriptase-based PCR ("RT-PCR") (See FIG. 3).

The 82 confirmed gene fragments represent 52 distinct genes, as several genes are represented by more than one differentially-expressed gene fragment. The expression of thirty-one genes had been previously reported to respond to PPARαL. However, of the 52 genes, a total of 17 genes that had previously been demonstrated to be PPARα-responsive in hepatic tissue were replicated by this method. Of these 17 genes, a total of 14 were modulated as previously reported. Three genes showed different modulation from previous reports: 1) acetyl-CoA-decarboxylase (+2-fold); apolipoprotein A-I (−2-fold); and steroid 3-delta-dehydrogenase (off).

The remaining fourteen genes previously shown to be PPARαL-responsive were not confirmed among the 82/218 bands analyzed. Of these, three genes (CYP4A6, 1-acylglycerophosphocholine acyltransferase and glycerol-3-phosphate acyltransferase) have no sequences available to query in GeneBank Rat. Four other genes (GRP78, carnitine palmitoyl transferase-1, apolipoprotein A-II and apolipoprotein C-III) represent mRNA's that would not be examined by this study because they were not cleaved by the RE combinations used. The remaining seven genes were previously determined by dosing other PPARαL over dose/time courses that differed from ours. Additionally, the identities of 136 GW9578-altered gene fragments were not confirmed. Finally, thirty-four confirmed genes were newly associated with PPARαL responsiveness. Twenty-five of these correspond to well-characterized rat genes or rat homologues of well-characterized human genes, while one represented an element of repetitive DNA. Eight were gene fragments novel to all species.

The differential expression of approximately 51 genes is demonstrated herein. This number represents one-third of all differentially expressed gene fragments so identified, and includes all fragments whose differential expression was greater than 5-fold. A total of 17 genes that had previously been demonstrated to be PPARα-responsive were detected by this method, including acyl-CoA oxidase, which regulates the rate limiting step in peroxisomal-oxidation of VLCFAs. Also disclosed is the identification of 34 differentially expressed genes that, previously, had not been associated with PPARαL response. Included among these genes is the very long chain acyl CoA synthetase (4-fold upregulated) and a novel isoform of acyl-CoA oxidase (10-fold upregulated). There has been no previous documentation of an association of VLCFA-CoA synthetase regulation with PPARαL response.

The changes in gene expression following administration of a PPARα ligand to rat cells are next discussed in more detail.

Increase in Acetyl-CoA Carboxylase levels After PPARαL Administration

Acetyl-CoA carboxylase, apolipoprotein A-I and steroid 3-delta-dehydrogenase genes were found to be modulated in an opposite manner to that reported previously. For example, acetyl CoA carboxylase activity was determined increase two-fold following PPARαL administration. Activity of this enzyme was previously reported to be reduced following the administration of a natural PPARα ligand, e.g., polyunsaturated fatty acids, and after co-incubation of hepatocytes with two older generation PPARαL ligands, namely, nafenopin or clofibrate (See, e.g., Willumsen, et al., 1993. *Lipids* 28:683–690; Tomazewski and Melnick, 1994. *Biochim Biophys Acta* 1220:119–124).

Polyunsaturated fatty acids are potent inhibitors of mRNA expression and enzyme activity for lipogenic enzymes, acetyl-CoA carboxylase, and fatty acid synthetase. Fatty acid synthetase possesses a fatty acid response element similar to the PPRE in its promoter region (See, e.g., Girard, et al., 1994. *FASEB J.* 8: 36–42). However, since such a fatty acid response element has not been documented in acetyl-CoA carboxylase, it is possible that older generation fibrates (e.g., nafenopin and clofibrate) may possess cross-reactivity with a second PUFA-responsive element that the newer generation of compounds putatively lack.

Reduction in Steroid 3-α-dehydrogenase Levels After PPARαligand Administration

The results disclosed herein demonstrate a highly significant 60-fold reduction in steroid 3-α-dehydrogenase transcript levels. Previously, steroid 3-α-dehydrogenase was reported to be upregulated by 1.8- to 2.4-fold by fibrates, e.g., benzafibrate, clinofibrate, clofibric acid, and fenofibric acid. In addition, clofibrate and Fenofibrate were demonstrated to act as weak inhibitors at physiological pH (See, e.g., Matsuura, el al., 1998. *J Pharmacol Exp Ther* 285: 1096–1103). However, the differences between the two experimental designs may account for the apparent discrepancy in experimental results. Additionally, the human data suggest that each fibrate/active metabolite combination may possess specific and differentiating effects upon the dehydrogenase. The GW9578 PPARαL ligand used herein may, like clofibrate or Fenofibrate, be inhibitory, but not metabolizable, at systemic physiological pH, thus resulting in the production of no stimulatory metabolite.

Changes in expression of fourteen genes previously shown to be PPARα-responsive were not detected. The genes encoding 1-acylglycerophosphocholine acyltransferase, cytochrome p450 4A6, and glycerol-3-phosphate acyltransferase did not have an equivalent rat mRNA sequences in the public sequence databases, and hence would not be earmarked for identification using the GENECALLING® sequence identification method. The genes encoding heat shock protein GRP78, carnitine palmitoyl transferase I, apolipoprotein A, and apolipoprotein CIII were found to produce mRNA sequences less than 500 bp in length using experimental protocols, and none of the sequences had predicted fragments from the 48 restriction enzyme (RE) pairs that were utilized in the GENECALLING® assays of the present invention. These sequences would similarly not be detected using the GENECALLING® sequence identification method.

Single nucleotide polymorphisms between a rat sequence deposited in GenBank and the rats utilized in the present invention may also cause the deletion of predicted restriction enzyme recognition sites. In the GENECALLING® assays used herein, a total of 136 differentially-expressed peaks could not to be identified. Hence, it may be reasonable to assume that some of these peaks represent novel sequence variants of the previously characterized known genes discussed supra.

PPARα-responsive Biochemical Pathways

A total of 34 genes which were not previously linked to PPARα activity were shown to be PPARαL-responsive; and of these genes, 23 are known rat genes with novel association. Of these 23 genes, 10 encode enzymes that function within biochemical pathways previously shown to be PPARα-responsive; and 6 encode enzymes that regulate multiple steps within biochemical pathways not previously PPARα-associated.

(i) Genes encodingfor enzymes involved in peroxisomal-oxidation

Active PPARα ligands induce peroxisome proliferation along with an increase in peroxisomal fatty acid α oxidation. Peroxisomal-oxidation is thus a primary target of the PPARαresponse. Genes for all three steps of this biochemical pathway have upregulated transcription (See, e.g., Marcus, et al., 1993, *Proc Natl Acad Sci USA* 90:5723–5727). The differential gene expression analyses herein confirm two of these steps: acyl-CoA oxidase and the enoyl-CoA hydratase/2-hydroxyl-CoA dehydrogenase. Additionally, six more genes encoding PPARα-responsive genes described herein are involved in the peroxisomal-oxidation cascade: (i) Very long chain acyl-CoA synthase; (ii) Carnitine octanoyl transferase; (iii) Acyl-CoA hydrolase; (iv) acyl-CoA thioesterase; (v) Catalase; and (vi) acyl-CoA oxidase variant. Very long chain acyl-CoA synthase is a peroxisome-specific acyl-CoA synthase responsible for preparing very long chain fatty acids for -oxidation. Carnitine octanoyl transferase translocates medium chain fatty acids across the peroxisomal membrane for subsequent degradation. Acyl-CoA hydrolase and acyl-CoA thioesterase are two genes responsible for modifications of acyl-CoAs and their release from fatty acid oxidation. Catalase is the enzyme responsible for neutralizing peroxide radicals, and was also upregulated. Another enzyme identified herein may be a novel acyl-CoA oxidase variant. This gene is of particular interest as it could indicate the presence of several acyl-CoA oxidases that might function in parallel during peroxisomal-oxidation.

The GENECALLING® assays demonstrate that both carnitine octanoyl transferase (the shuttle for medium chain fatty acids into the peroxisomes) and catalase (the free radical scavenger responsible for consuming the oxidative by-products of acyl-CoA oxidase) are upregulated by 4-fold and 12-fold, respectively.

(ii) Genes encoding for enzymes involved in mitochondrial fatty acid-oxidation

Mitochondrial-oxidation has been characterized as mildly responsive to PPARα stimuli. The treatment of rats with the PPARα ligand induced 24 enzymes related to fatty acid beta oxidation. Both in vivo and in vitro models of normolipidemic and hyperlipidemic rats treated with PPARαL show moderately up-regulated mitochondrial-oxidation (See, e.g., Hakkola, et al., 1994. *J Lipid Res* 35:1820–1828; Assimacopoulos-Jeannet, et al., 1991. *Am J Physiol* 260:R278–R283). Seven genes were found responsive to the treatment with PPARα ligand: (i) acylcarnitine translocase; (ii) long chain acyl-CoA dehydrogenase; (iii) short chain acyl-CoA dehydrogenase; (iv) bifunctional enzyme; (v) 3-ketoacyl-CoA thiolase; (vi) propionyl-CoA carboxylase; and (vii) a novel gene similar in sequence to mouse carnitine acetyltransferase, a protein responsible for the shuttle of medium chain fatty acids across both the mitochondrial and peroxisomal membranes. The novel gene is a moderately upregulated -oxidation enzyme following PPARα ligand treatment (FIG. 2). The results suggest that the hepatic lipid catabolism may be a molecular mechanism of action of the ligand for PPARα in liver.

(iii) Genes encoding for enzymes involved in microsomal fatty acid-oxidation

The cytochrome P450 4 (CYP4A) family encodes constitutive and inducible isozymes with functions in the fatty acid-oxidation. The expression of CYP4A1, CYP4A2 and CYP4A3 genes in liver and kidney is induced by peroxisome proliferators, which includes the hypolipidemic drug, clofibrate. Induction of CYP4A expression by clofibrate is due to transcriptional activation, mediated possibly via PPAR. Genes that encode CYP4A family of microsomal -hydroxylases contain PPREs (Aldridge et al., 1995 *Biochem J* 306: 473–479). The data also reveal that epoxide hydrolase (the enzyme immediately downstream of CYP4A2) was upregulated by 10-fold.

(iv) Genes encodingffor enzymes involved in ketogenesis

Ketogenesis is a process in the fatty acid catabolic pathway following -oxidation. Control of ketogenesis is exerted by transcriptional regulation of mitochondrial HMG-CoA synthase. Fatty acids increase transcription through PPRE, to which PPAR can bind. The gene encoding HMG-CoA synthetase, the rate-limiting enzyme in ketogenesis, contains a PPRE (See, e.g., Rodriguez, et al., 1994 *J Biol Chem* 269:18767–18772). The data provided herein demonstrate that acetoacetyl-CoA thiolase, the enzyme acting on the product of HMG-CoA synthetase, is upregulated by 100-fold by the PPARα ligand used in this study.

Together, these data for microsomal fatty acid -oxidation and ketogenesis support fatty acid catabolism as the major determinant of lowered triglycerides and VLDL following treatment with a ligand for peroxisome proliferator activated receptors.

(v) Genes encoding for enzymes involved in fatty acid synthesis

The role of hepatic fatty acid synthesis in PPARα ligand-activated liver tissue is controversial. One study in rat livers indicated it may be responsible for downregulating the three main components of fatty acid chain elongation (namely, ATP-citrate lyase, acetyl-CoA carboxylase, and fatty acid synthase) following administration of clofibrate (See, e.g., Willumsen et al., 1993 *Lipids* 28: 683–690). Yet, malic enzyme, the supplier of NADPH to the fatty acid synthesis engine, and stearyl-CoA desaturase, the enzyme that inserts -9 double bonds into $C_8$ saturated fatty acids. have PPREs and are upregulated by PPARα ligands (See, e.g., Castelein et al., 1993 *J Biol Chem* 269: 26754–26758, Miller and Ntambi 1996. *Proc Natl Acad Sci USA* 93: 9443–9448). The GENECALLING® sequence identification studies described herein show the upregulation of malic enzyme and stearyl-CoA desaturase upon treatment with PPARα ligand. In addition upregulation of acetyl-CoA carboxylase, the rate-limiting step of fatty acid synthesis, is also observed. This may suggest global upregulation of hepatic fatty acid synthesis by the novel PPARα ligand used in this invention. Differential regulation of ATP citrate lyase and fatty acid synthase were not detected in this analysis.

(vi) Genes encoding for enzymes involved in steroid catabolism and excretion

Clinically, fibrate compounds have shown modest efficacy in treating hypercholesterolemic patients (type IIa hyperlipidemia) with relatively little reduction in plasma LDL cholesterol. Accordingly, the transcription of six steroid enzymes involved in steroid catabolism and excretion were found to be regulated by PPARα. These enzymes included (i) steroid-3-α-dehydrogenase; (ii) hydroxysteroid sulfotransferase; (iii) CYP p450 M1; (iv) SMP-2; (v) 17-α-hydroxysteroid dehydrogenase IV; and (vi) UDP-glucosuronyl transferase 21. Interestingly, only 17-α-hydroxysteroid dehydrogenase IV was shown to be up-regulated by PPARαL, as was previously reported (See, e.g, Corton, et al., 1996. *Mol Pharmacol* 50:1157–1166). The genes encoding for the other steroid catabolism enzymes were downregulated by treatment with PPARαL.

Transcription of the PPARαL itself is regulated by the glucocorticoid receptor, another nuclear receptor. Previously, PPARα had also been implicated in immunomodulation through increased clearance or inhibition of inflammatory mediators (e.g., See, e.g., Devchand, et al., 1996. *Nature* 384:39–43; Staels, et al., 1998. *Nature* 393:790–793). However, the only potentially anti-inflammatory effects of PPARα that were detected in liver in this invention were the down-regulation of metallothionein 1 (i.e., 100-fold) and of steroid catabolic enzymes.

(vii) Genes encoding for enzymes involved in protoporphyrin IX biosynthesis

Protoporphyrin IX is the organic backbone for heme, a necessary constituent of redox enzymes like catalase and most cytochromes. This invention provides data for the upregulated transcription of mRNA for five individual cytochromes and catalase (See above). An increase in these proteins suggests stimulated heme synthesis since the catalytic subunit of the enzymes may require a heme group for activity. This invention discloses upregulation of two genes encoding for enzymes involved in protoporphyrin IX biosynthesis (d-aminolevulinate synthetase, and porphobilinogen deaminase). D-aminolevulinate synthetase and porphobilinogen deaminase were found to be up-regulated by 4-fold and 60-fold, respectively. This suggests that heme synthesis is being coordinately upregulated.

An additional clinical effect of the treatment with PPARα ligand is the reduction in atherogenic LDL lipid peroxides and slowing arterial intimal thickening. Upregulation of catalase and protoporphyrin synthesis by PPARα ligand treatment suggests a molecular mechanism for the decrease in oxidized lipid, which is believed to represent a beneficial atherosclerosis-inhibiting effect of PPARα ligand.

(viii) Genes encoding for proteins unrelated to metabolic pathways

The expression of six genes unrelated to metabolic pathways was also modified by PPARαligand. These genes include (i) histidine decarboxylase; (ii) Cytochrome p450, phenobarbital inducible [CYP2B1]; (iii) heat shock protein 60; (iv) Glutathione S transferase Ya subunit; (v) Dynein-like protein-3; and (vi) UDP-glucose pyrophosphorylase.

Histidine decarboxylase: The gene encoding for the enzyme responsible for converting histidine to histamine was upregulated by six-fold following exposure to PPARαligand in liver. Histidine decarboxylase was previously found to be upregulated in rat stomach following its exposure to ciprofibrate (>See, e.g., Waldum et al., 1998 *J. Mol. Endocrinol.* 20, 111–117). This upregulation was observed in concert with an increase in antral gastric G-cells for which histidine decarboxylase is a known marker.

Cytochrome p450, phenobarbital inducible [CYP2B1]: CYP2B1 is a member of a class of cytochromes responsible for metabolizing xenobiotics through monooxygenase pathways. The gene encoding for CYP2B1 has been shown to be upregulated in rat hepatocytes following treatment with clofibric acid, but has not been observed to change in an in vivo mouse model treated with clofibrate (See, e.g., Bars et al., 1993 Biochem. Pharmacol. 45, 2045–2053; Austin et al. 1995 Toxicology 97, 59–69).

Heat shock protein 60: Heat shock protein 60 is a mitochondrial molecular chaperone shown to have a suggested role in peroxisomal protein conformation (See, e.g., Soltys et al., Exp. Cell. Res. 222, 16–27 1996). A three-fold upregulation of hsp60 was detected following administration of GW9578. This observation supports a role for this protein as a chaperone in the folding of peroxisomal proteins.

Glutathione S transferase Ya subunit: The expression of the gene for glutathione S transferase Ya subunit was found to be three-fold decreased upon treatment with PPARα ligand. This decrease relates to the heptocarcinogenic feature of some PPARα ligands. A similar decrease in GSTa isoform was detected as a precancerous change in rat livers treated with atligand nafenopin (See, e.g., Grasl-Kraupp et al., 1993 Carcinogenesis 14, 2407–2412).

Dynein-like protein and UDP-glucose pyrophosphorylase: Two genes, dynein-like protein 3 and the rat homologue for UDP-glucose pyrophosphorylase had no previous associations to PPARα ligands or to their downstream metabolic or toxicologic effects. These are de novo associations for this class of molecules.

Remarkably, 29 of the 38 differentially-regulated genes encoding metabolic enzymes described herein support triglyceride metabolism, with none of these genes being involved in cholesterol biosynthesis. This correlation suggests an almost exclusive triglyceride profile for drug activity. The up-regulation of catalase/protoporphyrin synthesis suggests a direct molecular mechanism supporting the observed decrease in oxidized lipid peroxide content, a disease-modifying effect. Furthermore, all confirmed genes represent structural genes stipulating that PPARαL drives its own end-effect without intermediary signal transduction.

Based in part on the identification of PPARα ligand responsive nucleic acid sequences, the invention provides screening methods based on nucleic acid sequences responsive to PPARα ligands. Also provided are methods for diagnosing or assessing conditions associated with PPARα metabolism using genes differentially expressed in response to PPARα ligands, as well as methods of treating adrenoleukodystrophy using PPARα ligands. In other aspects, the invention provides nucleic acid collections for identifying agents and pathologies Associated with PPARα ligand responsive nucleic acid sequences. The invention additionally provides substrate arrays for identifying agents and pathologies associated with PPARα ligand responsive nucleic acid sequences, as well as single nucleotide polymorphisms associated with PPARα ligand responsive genes.

Screening Methods Based on Nucleic Acid Sequences Responsive to PPARα Ligands

In various aspects, the invention provides methods for screening for agents by examining the ability of a test agent to elicit a change in expression of one or more of the nucleic acid sequences described above. As is explained in more detail below, a candidate test agent is typically contacted with a test cell, and expression of one or more of the nucleic acid sequences in the test cell is measured. Expression of the sequences is then compared to expression of the sequences in a control cell, which is preferably similar to, or identical to, the test cell, but which has not been contacted with the test compound.

Thus, in one aspect, the invention provides a method of identifying a candidate therapeutic agent for a pathophysiology associated with a PPARα-mediated pathway. The method includes providing a cell capable of expressing one or more nucleic acids whose expression changes following addition to a cell of ligand for PPARα, such as the nucleic acid sequences described above. Thus, the nucleic acids can include nucleic acid sequences such as genes, e.g., those encoding carnitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and Glutathione transferase Ya subunit. Alternatively, or in addition, the nucleic acid can include one of the novel gene fragments described herein (SEQ ID NOS: 1–11).

Preferred cells are liver cells, or cell lines derived from liver cells. The cell can be of mammalian origin, e.g., from a human, rodent (such as, e.g., a rat or mouse), dog, cat, horse, cow, goat, rabbit, or pig. The cell can be provided either in vitro or ex vivo from a mammalian subject. The mammalian subject can be, e.g., a human, rodent (such as, e.g., a rat or mouse), dog, cat, horse, cow, goat, rabbit, or pig.

The cell is contacted with a candidate therapeutic agent and expression of one or more of the nucleic acid sequences is measured. In general, the test agent can be any compound or composition. The compound can be obtained, e.g., using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection.

Examples of methods for the synthesis of molecular libraries can be found in the art. These examples for example in: De Witt el al. (1993) *Proc Natl Acad Sci U.S.A.* 90:6909; Erb et al. (1994) *Proc Natl Acad Sci U.S.A.* 91:11422; Zuckermann el al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Expression of nucleic acid sequences can be measured at the RNA level, e.g., by measuring transcripts associated with the various nucleic acid sequences. For sequences associated with a polypeptide product, e.g., genes encoding the above-listed enzymes, expression can alternatively be measured by measuring levels of the polypeptide product. In general, any art-recognized method for detecting RNA or polypeptides can be used as long as it results in the specific detection of a transcript or translation product of the measured nucleic acid sequence.

Expression of the sequences in the presence of the test agent is then compared to the expression of the sequences in a control cell. In preferred embodiments, the control cell is a cell as similar as possible to the test cell, with the exception that the control cell is not exposed to the test agent. A convenient method of generating a control cell population is to divide a cell population, e.g., a liver cell population, into two subpopulations, and then administering the test agent to one of the subpopulations of cells.

An alteration in expression of the genes in the presence of the test agent compared to expression of the genes in a control cell not exposed to the test agent indicates the test agent is a candidate therapeutic agent for a pathophysiology associated with a PPARα-mediated pathway. The alteration in expression that is indicative of a candidate therapeutic agent depends on the particular gene whose expression is being measured, and will correspond to the alterations (i.e., upregulation or down regulation) reported above for the genes whose expression changes following addition of the GW9578 PPARα ligand.

Thus, for some nucleic acid sequences, a test agent will be considered a candidate therapeutic agent if it leads to an increase in expression of the nucleic acid sequence in the test cell compared to expression in the absence of the test agent. Examples of genes whose expression will increase include, e.g., amitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, acetoacetyl-CoA thiolase, 8-aminolevulinate synthase, porphobilinogen deaminase, histidine decarboxylase, cytochrome p450, phenobarbital inducible atalase; cynein-like protein 3, heat shock protein 60, and SEQ ID NOS: 1–11.

For other nucleic acid sequences, a test agent will be considered a candidate therapeutic agent if it leads to a decrease in expression. Nucleic acid sequences whose decrease in expression is indicative of a candidate therapeutic agent include, e.g., hydroxysteriod sulfotransferase, cytochrome p450 M1, androgen repressible liver protein SMP-2, UDP-glucosuronyl transferase-21, metallothionein-1; and glutathione transfcrase Ya subunit.

In some embodiments, alteration in expression of two or more of the nucleic acid sequences, e.g., 3, 4, 5, 10, 15, 20, 25, 30, or even all of the herein sequences disclosed can be examined. If desired, expression of sequences whose expression is newly correlated with PPARα ligands as described herein, can be measured along with sequences previously reported to be correlated with PPARα ligands. These sequences include, e.g., genes encoding long chain acyl CoA synthase, fatty acid transport protein, medium chain acyl-CoA dehydrogenase, HMG-CoA synthase, acyl-CoA oxidase, peroxisomal enoyl-CoA hydratase/3-hydroxyacyl CoA dehydrogenase, peroxisomal 3-ketoacyl-CoA thiolase, acyl-CoA hydrolase, acyl-CoA thioesterase, cytochrome p450 4A1, cytochrome p450 4A2, cytochrome p450 4A3, cytochrome p450 4A6, delta-3-delta-2 enoyl-CoA isomerase, acetyl CoA carboxylase, ATP citrate lyase, fatty acid synthase, flucose 6-phosphate dehydrogenase, glycerophosphate acyltransferase, malic enzyme, stearyl-CoA desaturase, hydroxysteroid dehydrogenase IV/bifunctional enzyme II, steroid 3a dehydrogenase, liver fatty acid binding protein, lipoprotein lipase, apolipoprotein A1, apolipoprotein A2, apolipoprotein C3, 1-acylglycerophosphocholine acyltransferase, carnitine palmitoyl transferase-1, and heat shock protein GRP78.

This method, including its various embodiments, can also be used to identifying a ligand for a PPARα. A cell capable of expressing one of the differentially expressed nucleic acids is contacted with a test agent expression, expression of one or more of the nucleic acids is measured. An alteration in expression of the nucleic acids in the presence of the test agent compared to expression of the genes in a control cell not exposed to the test agent indicates the test agent is a ligand for a PPARα.

In another aspect, the invention features a method of identifying a candidate therapeutic agent for a pathophysiology associated with a PPARα-mediated pathway. In this method, a test agent is contacted with polypeptide encoded by one the differentially expressed nucleic acids. These polypeptides can include, e.g., carnitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and glutathione transferase Ya subunit. Binding of the test agent to one or more of the polypeptides is determined. Binding of the test agent to the polypeptide indicates that the test agent is a candidate therapeutic agent for a pathophysiology associated with a PPARα x-mediated pathway.

The test agent can include any compound or composition. Libraries of compounds can may be presented in solution (e.g., Houghten (1992) *Biotechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991 ) *J Mol Biol* 222:301–310; Ladner above.).

In some embodiments, binding between a test agent and a polypeptide includes determining the ability of the test compound to modulate (e.g., stimulate or inhibit) the activity of the polypeptide or polypeptides, or one or more biologically active portions thereof. Determining the ability of the test agent to modulate activity can be accomplished, for example, by determining the ability of the polypeptides to bind to or interact with a target molecule of the particular polypeptide being tested. As used herein, a "target molecule" is a molecule with which a TorC protein binds or interacts in nature, for example, a molecule associated with the internal surface of a cell membrane or a cytoplasmic molecule. A target molecule can be one of the herein described differentially expressed polypeptides, or can be another polypeptide. The target, for example, can be a second intercellular protein that has catalytic activity or a protein that facilitates the association of downstream signaling molecules with these polypeptides.

In some embodiments, determining the ability of a test agent to bind to a polypeptide can be accomplished by determining the activity of a target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a torC-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting one or more of the above described differentially expressed polypeptides, or biologically active portions thereof, with a test agent and determining the ability of the test compound to bind to the polypeptide fragment. Binding of the test compound to the test polypeptide can be determined either directly or indirectly.

In another embodiment, an assay is a cell-free assay comprising contacting one or more polypeptides or biologically active portion thereof with a test compound and determining the ability of the test compound to modulate (e.g., stimulate or inhibit) its activity. For example, the catalytic/enzymatic activity of the target molecule on an appropriate substrate can be determined.

In yet another embodiment, the cell-free assay comprises contacting one or more polypeptides, or biologically active portions thereof, with a known compound which binds to the polypeptides to form an assay mixture, contacting the assay mixture with a test agent, and determining the ability of the test agent to interact with the polypeptides. Determining the ability of the test compound to interact with a polypeptide is based on determining the ability of the polypeptide to preferentially bind to or modulate the activity of the known compound.

The cell-free assays of the present invention are amenable to use of both soluble forms or the membrane-bound forms of polypeptides. In the case of cell-free assays comprising the membrane-bound forms, it may be desirable to utilize a solubilizing agent such that the membrane-bound form is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-(3-cholamidopropyl)dimethylamminiol-1-propane sulfonate (CHIAPS), 3-(3-cholamidopropyl)dimethylamminiol-2-hydroxy-1-propane sulfonate (CHAPSO), or N-dodecyl--N,N-dimethyl-3-ammonio-1-propane sulfonate.

In more than one embodiment of the above assay methods of the present invention, it may be desirable to immobilize either the polypeptides or the test agent to facilitate separation of complexed from uncomplexed forms of one or both of the proteins, as well as to accommodate automation of the assay. Binding of a polypeptide to the test agent, or interaction of the polypeptide with a target molecule in the presence and absence of a test agent, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-torC fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or test polypeptide, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of polypeptide binding or activity determined using standard techniques.

Other techniques for immobilizing proteins on matrices can also be used in the screening assays of the invention. For example, either a test polypeptide or its target molecule can be immobilized utilizing conjugation of biotin and streptavidin. Biotinylated polypetpides or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a test polypeptide or target molecules, but which do not interfere with binding of the polypeptide to its target molecule, can be derivatized to the wells of the plate, and unbound target or polypeptide rapped in the wells by antibody conjugation.

Methods for detecting such complexes, in addition to those described above for the GST-immobilized complexes, include immunodetection of complexes using antibodies reactive with the test polypeptide or target molecule, as well as enzyme-linked assays that rely on detecting an enzymatic activity associated with the polypeptide or target molecule.

The invention also provides in vivo screening methods. Accordingly, in a further aspect, the invention includes a method of identifying a candidate therapeutic agent for a pathophysiology associated with a PPARα-mediated pathway. In this method, an agent is administered to a first mammal, i.e., a test mammal after which a cell sample from the first mammal is removed. A second cell sample is also obtained from a second mammal, i.e., a control mammal, to which the agent has not been administered. The cell samples preferably include in whole or in part liver cells.

If desired, a control composition, e.g., a vehicle lacking the test agent, is administered to the second mammal. Differential gene expression in the first and second cell samples of one or more genes encoding a polypeptide selected from the group consisting of is then assessed. A determination that one or more of the genes is differentially expressed indicates the agent is a candidate therapeutic agent for a pathophysiology associated with a PPARα-mediated pathway.

In preferred embodiments, differential gene expression is determined using GENECALLING® sequence analysis. The examined sequences can include, e.g., sequences encoding long cha in acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolaset cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21. metallothionein-1 and Glutathione transferase Ya subunit. Alternatively, or in addition, the nucleic acid can include one of the novel gene fragments described herein (SEQ ID NOS: 1–11).

In preferred embodiments, the first and second mammals are rodents, e.g., rats or mice. Preferably, the first and second mammals are matched to be as identical as possible,. Thus, the first and second mammals are preferably matched for such parameters as, e.g., age, sex, mass, and genetic background. In some embodiments, the first and second mammals are siblings, e.g., litter mates.

In another aspect, the invention provides a method of determining whether a candidate therapeutic agent has PPARα-specific ligand binding activity. The method includes administering the agent to a first mammal ("test animal") and obtaining a cell sample from the mammal. A second cell sample is also obtained from a second mammal ("control animal"), which has not been administered the agent. If desired, a control composition, e.g., a vehicle lacking the test agent, is administered to the control animal.

Nucleic acid expression is then assessed in the two cell samples, using, e.g., GENECALLING® sequence identification. Determining that one or more of the genes is differentially expressed in the first and second samples indicates the agent has a PPARα-specific ligand binding activity.

The nucleic acids whose expression is measured in the two samples can include, e.g., sequences encoding long chain acyl-CoA dehydrogenase. short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and Glutathione transferase Ya subunit. Alternatively, or in addition, the nucleic acid can include one of the novel gene fragments described herein (SEQ ID NOS: 1–11).

In a still further aspect, the invention includes a method of screening a candidate pharmaceutical agent for effect or activity for a PPARα-associated gene product. An agent is administered to a first, or test, mammal, after which a first cell sample is obtained therefrom. A second cell sample is also obtained from a second, or control, mammal. If desired, a control composition, e.g., a vehicle lacking the test agent, is administered to the control animal.

Differential expression of a PPARα-associated gene is then assessed in the first and second cell samples using e.g., the GENECALLING® sequence identification method. A difference in expression of the PPARα gene in the first and second samples indicates that the agent has an effect or activity for the PPARα-associated gene product.

In some embodiments, the expression pattern detected with a particular nucleic acid sequence is similar to or identical to the expression pattern detected with the nucleic acid sequence following administration of GW9578 to a test sample vs. control sample.

In still further aspect, the invention provides a method of screening a candidate pharmaceutical agent as a potential ligand for a PPARα-associated gene product. The method includes administering the agent to a first mammal ("test animal") and obtaining a cell sample from the first mammal after administering the agent. A second cell sample is also obtained from a second mammal ("control mammal"). Expression of one or more PPARα-associated genes in the first and second cell samples is then compared. A difference in expression in the first and second samples indicates that the agent is a potential ligand for a PPARα-associated gene product.

The nucleic acids whose expression is measured in the two samples can include, e.g., sequences encoding long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and Glutathione transferase Ya subunit. Alternatively, or in addition, the nucleic acid can include one of the novel gene fragments described herein (SEQ ID NOS: 1–11).

In another aspect, the invention includes a method of determining whether a candidate pharmaceutical agent has PPARα-specific ligand activity. The method includes generating a differential gene expression profile that is induced by administration of the agent to a mammal and comparing the profile to a differential gene expression profile of a plurality of nucleic acid sequences known to be differentially expressed when a PPARα-specific ligand is administered to another member of the same species of the mammal. A similarity in the expression profile indicates that the agent has PPARα-specific ligand binding activity.

The plurality of nucleic acid sequences can include, e.g., two or more nucleic acids encoding long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and glutathione transferase Ya subunit. Alternatively, or in addition, the nucleic acid can include one of the novel gene fragments described herein (SEQ ID NOS: 1–11).

The invention also provides a method of determining the efficacy of an agent as a therapeutic agent in a pathology related to the expression of a PPARα-associated gene product. The method includes administering an agent modulating the expression of one or more PPARα-associated gene products to a subject, e.g. a human, suffering from, or suspected of being prone to develop, a pathology related to the expression of a PPARα-associated gene product. A cell sample is then obtained from the subject and expression of one or more PPARα-associated gene products in the sample is assessed in order to generate a gene expression profile in the subject for the agent. The gene expression profile is then compared to a reference gene expression profile previously determined to represent levels characteristic of therapeutic effectiveness. A correspondence in the gene expression profile in the sample to the reference gene expression profile indicates the agent is efficacious in treating a pathology related to the expression of a PPARα-associated gene product.

In a further aspect, the invention provides a method of determining an effective dosing regimen of an agent as a therapeutic agent in a pathology related to the expression of a PPARα-associated gene product. The method includes administering the agent to a subject, e.g., a human, suffering from, or suspected of being prone to develop, a pathology related to the expression of a PPARα-associated gene product and obtaining a cell sample from the subject. Gene expression of one or more PPARα-associated gene products in the sample relative to expression products in the absence of the agent is assessed in order to generating a gene expression profile in the subject for the agent. The gene expression profile is then compared to a gene expression profile previously determined to represent levels characteristic of therapeutic effectiveness. The agent can then be readministered, and additional gene expression profiles can be generated until the gene expression profile corresponds to the gene expression profile previously determined to represent levels characteristic of therapeutic effectiveness, thus establishing an effective dosing regimen of the agent as a therapeutic agent in a pathology related to the expression of a PPARα-associated gene product can be determined.

In a further aspect, the invention provides a method of identifying a candidate pharmaceutical agent that selectively induces PPARα-ligand activity. The method includes obtaining a first tissue sample from a mammal known to express preferentially the PPARα and a second tissue sample from the mammal known to express preferentially the PPARγ. The first tissue sample and the second tissue samples are contacted with a test agent. Differential gene expression profiles are then created in the first and second samples and compared to gene expression samples in respective control tissue samples not exposed to the agents. A differential gene expression pattern characteristic of a PPARα-ligand in the first sample and a differential gene expression pattern not characteristic of a PPARα-ligand in the second sample indicates that the compound selectively induces specific PPARα-ligand activity.

Methods of Diagnosing Conditions Associated with PPARα Metabolism Using Genes Differentially Expressed in Response to PPARα Ligands The invention also provides a method of diagnosing a pathophysiology associated with a PPARα-mediated pathway in a subject. The method includes providing a cell from the subject. The cell is capable of expressing a nucleic acid whose expression is differentially regulated in response to a PPARα ligand. Expression of the nucleic acid sequences is measured, and an alteration in expression of the genes as compared to the expression of the genes in a control cell indicates that the subject has a pathophysiology associated with a PPARα-mediated pathway.

The control cell is provided from a subject who does not have, or is not suspected of having, the pathophysiology. Thus, the sample can be from, e.g., a similarly matched (with respect to age, sex, or genetic background) separate individual. Alternatively, the control sample can be a cell from the same subject at a time when the subject does not have the pathophysiology.

The subject can be e.g., a human, rodent (such as, e.g., a rat or mouse), dog, cat, horse, cow, goat, rabbit, or pig. Preferably, the examined cell is a liver cell.

The nucleic acid sequences can include, e.g., genes, e.g., those encoding carnitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase. propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and Glutathione transferase Ya subunit. Alternatively, or in addition, the nucleic acid can include one of the novel gene fragments described herein (SEQ ID NOS: 1–11).

Expression of nucleic acid sequences can be measured at the RNA level, e.g., by measuring transcripts associated with the various nucleic acid sequences. For sequences associated with a polypeptide product, e.g., genes encoding the above-listed enzymes, expression can alternatively be measured by measuring levels of the polypeptide product. In general, any art-recognized method for detecting RNA or polypeptides can be used as long as it results in the specific detection of a transcript or translation product of the measured nucleic acid sequence.

An alteration in expression of the genes in the test sample compared to expression of the genes in a control cell not exposed to the test agent indicates the subject suffers from, or is at risk for, a pathophysiology associated with a PPARα-mediated pathway.

In some embodiments, alteration in expression of two or more of the nucleic acid sequences, e.g., 3, 4, 5, 10, 15, 20, 25, 30, or even all of the herein sequences disclosed can be examined. If desired, expression of sequences whose expression is newly correlated with PPARα ligands as described herein, can be measured along with sequences previously reported to be correlated with PPARα ligands. These sequences include, e.g., genes encoding long chain acyl CoA synthase, fatty acid transport protein, medium chain acyl-CoA dehydrogenase, HMG-CoA synthase, acyl-CoA oxidase, peroxisomal enoyl-CoA hydratase/3-hydroxyacyl CoA dehydrogenase, peroxisomal 3-ketoacyl-CoA thiolase, acyl-CoA hydrolase, acyl-CoA thiocsterase, cytochrome p450 4A1, cytochrome p450 4A2, cytochrome p450 4A3, cytochrome p450 4A6, delta-3-delta-2 enoyl-CoA isomerase, acetyl CoA carboxylase, ATP citrate lyase, fatty acid synthase, flucose 6-phosphate dehydrogenase, glycerophosphate acyltransferase, malic enzyme, stearyl-CoA desaturase, hydroxysteroid dehydrogenase IV/bifunctional enzyme II, steroid 3a dehydrogenase, liver fatty acid binding protein, lipoprotein lipase, apolipoprotein A1, apolipoprotein A2, apolipoprotein C3, 1-acylglycerophosphocholine acyltransferase, carnitine palmitoyl transferase-1, and heat shock protein GRP78.

The invention also includes a method of assessing the efficacy of a treatment for a pathophysiology associated with a PPARα-mediated pathway in a subject. The method includes providing a cell from a subject exposed to the treatment and measuring the expression of PPARα regulated nucleic acid sequences in the cell. An alteration in expression of the nucleic acids in the cell compared to expression of the nucleic acids in a cell from the subject prior to, or earlier in treatment, or in a control cell not exposed to said treatment, indicates said treatments is efficacious.

The subject can be, e.g, a human, rodent (such as, e.g., a rat or mouse), dog, cat, horse, cow, goat, rabbit, or pig. Preferably, the examined cell is a liver cell.

The nucleic acid sequences can include, e.g., genes, e.g., those encoding carnitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and Glutathione transferase Ya subunit. Alternatively, or in addition, the nucleic acid can include one of the novel gene fragments described herein (SEQ ID NOS: 1–11).

Expression of nucleic acid sequences can be measured at the RNA level, e.g., by measuring transcripts associated with the various nucleic acid sequences. For sequences associated with a polypeptide product, e.g., genes encoding the above-listed enzymes, expression can alternatively be measured by measuring levels of the polypeptide product. In general, any art-recognized method for detecting RNA or polypeptides can be used as long as it results in the specific detection of a transcript or translation product of the measured nucleic acid sequence.

An alteration in expression of the genes in the test sample compared to expression of the genes in the control cell indicates treatment is efficacious. The alteration in expression that is indicative of efficaciousness depends on the particular gene whose expression is being measured, and will correspond to the alterations (i.e., upregulation or down regulation) reported above for the genes whose expression changes following addition of the GW9578 PPARα ligand.

Thus, for some nucleic acid sequences, treatment will be considered efficacious in some embodiments if the tested nucleic acid sequence is expressed at increased levels in the test cell compared to expression in the control cell. Examples of genes whose expression will be increased include, e.g., carnitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, acetoacetyl-CoA thiolase, 8-aminolevulinate synthase, porphobilinogen deaminase, histidine decarboxylase, cytochrome p450, phenobarbital inducible atalase; cynein-like protein 3, heat shock protein 60, and SEQ ID NOS:1–11.

For other nucleic acid sequences, a sample will be considered efficacious in some embodiments if the tested nucleic acid shows decreased expression relative to a control. Nucleic acid sequences whose increase in expression is indicative of a diseased state include, e.g., hydroxysteriod sulfotransferase, cytochrome p450 M1, androgen repressible liver protein SMP-2, UDP-glucosuronyl transferase-21, metallothionein-1; and glutathione transferase Ya subunit.

In some embodiments, alteration in expression of two or more of the nucleic acid sequences, e.g., 3, 4, 5, 10, 15, 20, 25, 30, or even all of the herein sequences disclosed can be examined. If desired, expression of sequences whose expression is newly correlated with PPARα ligands as described herein, can be measured along with sequences previously reported to be correlated with PPARα ligands. These sequences include, e.g., genes encoding long chain acyl CoA synthase. fatty acid transport protein, medium chain acyl-CoA dehydrogenase, HMG-CoA synthase, acyl-CoA oxidase, peroxisomal enoyl-CoA hydratase/3-hydroxyacyl CoA dehydrogenase, peroxisomal 3-ketoacyl-CoA thiolase, acyl-CoA hydrolase, acyl-CoA thioesterase, cytochrome p450 4A1, cytochrome p450 4A2, cytochrome p450 4A3, cytochrome p450 4A6, delta-3-delta-2 enoyl-CoA isomerase, acetyl CoA carboxylase, ATP citrate lyase, fatty acid synthase, flucose 6-phosphate dehydrogenase, glycerophosphate acyltransferase, malic enzyme, stearyl-CoA desaturase, hydroxysteroid dehydrogenase IV/bifunctional enzyme II, steroid 3a dehydrogenase, liver fatty acid binding protein, lipoprotein lipase, apolipoprotein A1, apolipoprotein A2, apolipoprotein C3, 1-acylglycerophosphocholine acyltransferase, carnitine palmitoyl transferase-1, and heat shock protein GRP78.

In another aspect, the invention provides a method for selecting a therapeutic agent for treatment of a pathophysiology associated with a PPARα-mediated pathway in a subject. The method includes providing a cell that is capable of expressing a PPAR a ligand-responsive nucleic acid from the subject, contacting said cell with a test agent, and measuring expression of the gene expressing said polypeptide in said subject. An alteration in expression of the nucleic acid in the cell compared to expression of the nucleic acid in a control cell not exposed to the test agent indicates said test agent is a therapeutic agent for treatment of a pathophysiology associated with a PPARα-mediated pathway in the subject.

The subject can be e.g., a human, rodent (such as, e.g., a rat or mouse), dog, cat, horse, cow, goat, rabbit, or pig. Preferably, the examined cell is a liver cell.

The nucleic acid sequences can include, e.g., genes, e.g., those encoding carnitine/acyl carnitine carrier protein, long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, cetoacetyl-CoA thiolase, 8-aminolevulinate synthase, porphobilinogen deaminase, histidine decarboxylase, cytochrome p450, phenobarbital inducible; catalase, dynein-like protein 3, heat shock protein 60, hydroxysteriod sulfotransferase, cytochrome p450 M1, androgen repressible liver protein SMP-2, UDP-glucosuronyl transferase-21, metallothionein-1 and Glutathione transferase Ya subunit. Alternatively, or in addition, the nucleic acid can include one of the novel gene fragments described herein (SEQ ID NOS: 1–11).

Expression of nucleic acid sequences can be measured at the RNA level, e.g., by measuring transcripts associated with the various nucleic acid sequences. For sequences associated with a polypeptide product, e.g., genes encoding the above-listed enzymes, expression can alternatively be measured by measuring levels of the polypeptide product. In general, any art-recognized method for detecting RNA or polypeptides can be used as long as it results in the specific detection of a transcript or translation product of the measured nucleic acid sequence.

An alteration in expression of the genes in the test sample compared to expression of the genes in the control cell indicates treatment is a suitable therapeutic agent for use in the subject. The alteration in expression that is indicative of a suitable agent depends on the particular gene whose expression is being measured, and will correspond to the alterations (i.e., upregulation or down regulation) reported above for the genes whose expression changes following addition of the GW9578 PPARα ligand.

Thus, for some nucleic acid sequences, an agent will be considered suitable if the tested nucleic acid sequence is expressed at increased levels in the test cell compared to expression in the control cell. Examples of genes whose expression will be increased include, e.g., carnitine/acyl carnitine carrier protein. long chain acyl-CoA dehydrogenase, short chain acyl CoA dehydrogenase, long chain enoyl-CoA hydratase/3-hydroxyacyl-CoA dehydrogenase, long chain ketoacyl-CoA thiolase, propionyl-CoA carboxylase, very long chain acyl-CoA synthetase, carnitine octanoyl transferase, epoxide hydrolase, acetoacetyl-CoA thiolase, 8-aminolevulinate synthase, porphobilinogen deaminase, histidine decarboxylase, cytochrome p450, phenobarbital inducible atalase; cynein-like protein 3, heat shock protein 60, and SEQ ID NOS:1–11.

For other nucleic acid sequences, an agent will be considered suitable if the tested nucleic acid shows decreased expression relative to a control. Nucleic acid sequences whose increase in expression is indicative of a diseased state include, e.g., hydroxysteriod sulfotransferase, cytochrome p450 M1, androgen repressible liver protein SMP-2, UDP-glucosuronyl transferase-21, metallothione-in-1; and glutathione transferase Ya subunit.

In some embodiments, alteration in expression of two or more of the nucleic acid sequences, erg., 3, 4, 5, 10, 15, 20, 25, 30, or even all of the herein sequences disclosed can be examined. If desired, expression of sequences whose expression is newly correlated with PPARα ligands as described herein, can be measured along with sequences previously reported to be corrclated with PPARα ligands. These sequences include, e.g, genes encoding long chain acyl CoA synthase, fatty acid transport protein, medium chain acyl-CoA dehydrogenase, HMG-CoA synthase, acyl-CoA oxidase, peroxisomal enoyl-CoA hydratase/3-hydroxyacyl CoA dehydrogenase, peroxisomal 3-ketoacyl-CoA thiolase, acyl-CoA hydrolase, acyl-CoA thioesterase, cytochrome p450 4A1, cytochrome p450 4A2, cytochrome p450 4A3, cytochrome p405 4A6, delta-3-delta-2 enoyl-CoA isomerase, acetyl CoA carboxylase, ATP citrate lyase, fatty acid synthase, flucose 6-phosphate dehydrogenase, glycerophosphate acyltransferase, malic enzyme, stearyl-CoA desaturase, hydroxysteroid dehydrogenase IV/bifunctional enzyme II, steroid 3a dehydrogenase, liver fatty acid binding protein, lipoprotein lipase, apolipoprotein A1, apolipoprotein A2, apolipoprotein C3, 1-acylglycerophosphocholine acyltransferase, carnitine palmitoyl transferase-1, and heat shock protein GRP78.

Treatment of Adrenoleukodystrophy Using PPARαligands

The invention also provides a method of treating, preventing or delaying the onset of adrenoleukodystrophy. The method includes administering to a subject e.g., a human, in which such treatment or prevention is desired an effective amount of a therapeutic agent ("Therapeutic"). In some embodiments, the agent binds preferentially to a PPARα relative to a PPARγ. The agent can be, e.g., a fibrate derivative. In preferred embodiments, the agent is GW9578.

The therapeutic methods described herein are based in part on Applicants' discovery that PPARα ligand increases expression of acyl CoA oxidase, a novel acyl CoA oxidase-related gene, and very long chain fatty acid (VLCFA) CoA synthase, e.g,. 4-fold increase in very-long chain acyl-CoA synthase following exposure to the PPARαL. This indicates that this compound, or related PPARα ligands, is efficacious in the treatment of adrenoleukodystrophy (ALD). This X-linked disorder has an incidence of approximately 1 in 100,000, is often fatal, and is associated with impaired peroxisomal beta oxidation of VLCFA.

Therapeutics, e.g., therapeutic agents, of the present invention may be assayed by any method known within the art for efficacy in treating or preventing hypertriglyceridemia, in particular in adrenoleukodystrophy, and related disorders. Such assays include, but are not limited to, in vitro assays, as well as in vivo assays using animal models of hypertriglyceridemia, and in particular of adrenoleukodystrophy.

Once a hypertriglyceridemia, in particular in an adrenoleukodystrophy, has been shown to be amenable to treatment by way of modulating (i.e., inhibiting, antagonizing or agonizing) activity, the hypertriglyceridemia, in particular in adrenoleukodystrophy, may subsequently be treated or prevented by the administration of a Therapeutic that serves to modulate protein function.

The invention present discloses methods of treatment and prophylaxis by the administration to a subject of a pharmaceutically-effective amount of a Therapeutic of the invention. In a preferred embodiment, the Therapeutic is substantially purified and the subject is a mammal, and most preferably, human.

A protein of the present invention (derived from whatever source defined herein, including without limitation from recombinant and non-recombinant sources), as well as agents identified herein, e.g., agents identified as ligands of PPARα, or effectors of PPARα activity, may be used in a pharmaceutical composition when combined with a pharmaceutically acceptable carrier. Such compositions comprise a therapeutically-effective amount of a Therapeutic, and a pharmaceutically acceptable carrier. Such a composition may also be comprised of (in addition to protein and a carrier) diluents, fillers, salts, buffers, stabilizers, solubilizers, and other materials well known in the art. As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration.

A protein of the present invention may be active in multimers (e.g., heterodimers or homodimers) or complexes with itself or other proteins. As a result, pharmaceutical compositions of the invention may comprise a protein of the invention in such multimeric or complexed form.

Methods of administration include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or pre-neoplastic tissue.

Various delivery systems are known and can be used to administer a Therapeutic of the present invention including, e.g.: (i) encapsulation in liposomes, microparticles, microcapsulcs; (ii) recombinant cells capable of expressing the Therapeutic; (iii) receptor-mediated endocytosis (See, e.g., Wu and Wu, 1987. *J Biol Chem* 262:4429–4432); (iv) construction of a Therapeutic nucleic acid as part of a retroviral or other vector, and the like. In one embodiment of the present invention, the Therapeutic may be delivered in a vesicle, in particular a liposome. In a liposome, the protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028; and 4,737,323, all of which are incorporated herein by reference. In yet another embodiment, the Therapeutic can be delivered in a controlled release system including, e.g.: a delivery pump (See, e.g., Saudek, et al., 1989. *New Engl J Med* 321:574 and a semi-permeable polymeric material (See, e.g., Howard, et al., 1989. *J Neurosurg* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. *Proc Natl Acad Sci USA* 88:1864–1868), and the like. Alternatively, a nucleic acid Therapeutic can be introduced intracellularly and incorporated within host cell DNA for expression, by homologous recombination.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. However, suitable dosage ranges for intravenous administration of the Therapeutics of the present invention are generally about 20–500 micrograms (g) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Polynucleotides of the present invention can also be used for gene therapy. Gene therapy refers to therapy that is performed by the administration of a specific nucleic acid to a subject. Delivery of the Therapeutic nucleic acid into a mammalian subject may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. Polynucleotides of the invention may also be administered by other known methods for introduction of nucleic acid into a cell or organism (including, without limitation, in the form of viral vectors or naked DNA). Any of the methodologies relating to gene therapy available within the art may be used in the practice of the present invention. See e.g., Goldspiel, et al., 1993. *Clin Pharm* 12:488–505.

Cells may also be cultured ex vivo in the presence of therapeutic agents or proteins of the present invention in order to proliferate or to produce a desired effect on or activity in such cells. Treated cells can then be introduced in vivo for therapeutic purposes.

Kits and Nucleic Acid Collections for Identifying Agents and Pathologies Associated with PPARα Ligand Responsive Nucleic Acid Sequences In another aspect, the invention provides a kit useful for examining a pathophysiology associated with a PPARα-mediated pathway. The kit can include two or more PPARα ligand responsive nucleic acid sequences. These sequences include, e.g., nucleic acid sequences encoding carnitine/acyl carnitine carrier protein; Long chain acyl-CoA dehydrogenase; Short chain acyl CoA dehydrogenase; Long chain enoyl-CoA hydratase/3-hydroxyacyl-CoA dehydrogenase; Long chain ketoacyl-CoA thiolase; Propionyl-CoA carboxylase; Very long chain acyl-CoA synthetase; Carnitine octanoyl transferase; Epoxide hydrolase; Acetoacetyl-CoA thiolase; 8-aminolevulinate synthase; Porphobilinogen deaminase; Histidine decarboxylase; Cytochrome p450; phenobarbital inducible; Catalase; Dynein-like protein 3; Heat shock protein 60; Hydroxysteriod sulfotransferase; Cytochrome p450 M1; Androgen repressible liver protein SMP-2; UDP-glucosuronyl transferase-21; Metallothionein-1; Glutathione transferase Ya subunit, or sequences such as SEQ ID NOS: 1–11.

The kits may optionally include one or more nucleic acids encoding long chain acyl CoA synthase; fatty acid transport protein; medium chain acyl-CoA dehydrogenase; HMG-CoA synthase; acyl-CoA oxidase; peroxisomal enoyl-CoA hydratase/3-hydroxyacyl CoA dehydrogenase; peroxisomal 3-ketoacyl-CoA thiolase; acyl-CoA hydrolase; acyl-CoA thioesterase; cytochrome p450 4A1; cytochrome p450 4A2; cytochrome p450 4A3; cytochrome p450 4A6; delta-3-delta-2 enoyl-CoA isomerase; acetyl CoA carboxylase; ATP citrate lyase; fatty acid synthase; flucose 6-phosphate dehydrogenase; glycerophosphate acyltransferase; malic enzyme; stearyl-CoA desaturase; hydroxysteroid dehydrogenase IV/bifunctional enzyme II; steroid 3a dehydrogenase; liver fatty acid binding protein; lipoprotein lipase;

apolipoprotein A1; apolipoprotein A2; apolipoprotein C3; 1-acylglycerophosphocholine acyltransferase; carnitine palmitoyl transferase-1; and heat shock protein GRP78.

In preferred embodiments, the kit includes 3, 4, 5, 6, 8, 10, 12, 15, 20, 25, 30, 35, or all of the encoded nucleic acid sequences.

The invention also includes an isolated plurality of PPARα responsive nucleic acid sequences. The plurality typically includes two or more of the nucleic acid sequence selected from the group consisting of sequences encoding Carnitine/acyl carnitine carrier protein; Long chain acyl-CoA dehydrogenase; Short chain acyl CoA dehydrogenase; Long chain enoyl-CoA hydratase/3-hydroxyacyl-CoA dehydrogenase; Long chain ketoacyl-CoA thiolase; Propionyl-CoA carboxylase; Very long chain acyl-CoA synthetase; Carnitine octanoyl transferase; Epoxide hydrolase; Acetoacetyl-CoA thiolase; 8-aminolevulinate synthase; Porphobilinogen deaminase; Histidine decarboxylase; Cytochrome p450; phenobarbital inducible; Catalase; Dynein-like protein 3; Heat shock protein 60; Hydroxysteriod sulfotransferase; Cytochrome p450 M1; Androgen repressible liver protein SMP-2; UDP-glucosuronyl transferase-21; Metallothionein-1; Glutathione transferase Ya subunit, sequences comprising SEQ ID NOS: 1–10 and SEQ ID NO:11.

An "isolated" nucleic acid molecule is one that is separated from other nucleic acid molecules which are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. In various embodiments, the isolated nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, or a complement of any of these nucleotide sequences, can be isolated using standard molecular biology techniques and the sequence information provided herein. Using all or a portion of the nucleic acid sequences encoding the above-described proteins or nucleic acid sequences as hybridization probes, additional nucleic acid sequences can be isolated using standard hybridization and cloning techniques (e.g., as described in Sambrook et al., eds., Molecular Cloning: A Laboratory Manual $2^{nd}$ Ed., Cold Spring Harbor Laboratory Press, Cold Spring Harbor, N.Y., 1989; and Ausubel, et al., eds., Current Protocals in Molecular Biology, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the herein disclosed nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having at least about 10 nt. and as many as 50 nt., preferably about 15 nt. to 30 nt. TIhey may be chemically synthesized and may be used as probes.

In another embodiment, an isolated nucleic acid molecule of the invention comprises a nucleic acid molecule that is a complement of the herein disclosed nucleic acid sequences. A nucleic acid molecule that is complementary to the nucleotide sequence shown herein is one that is sufficiently complementary to the nucleotide sequences shown that it can hydrogen bond with little or no mismatches to the disclosed nucleotide sequences, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

The plurality of nucleic acids and kits described herein in some embodiments comprise only a portion of the nucleic acid sequences, e.g., a fragment. Fragments provided herein are defined as sequences of at least 6 (contiguous) nucleic acids or at least 4 (contiguous) amino acids, a length sufficient to allow for specific hybridization in the case of nucleic acids. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 45%, 50%, 70%, 80%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, el al., Current Protocols in Molecular Biology, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appi. Math., 1981,2: 482–489, which in incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of the herein described polypeptides. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for polypeptides of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein.

The plurality may optionally include one or more nucleic acids encoding polypeptides selected from the group consisiting of long chain acyl CoA synthase; fatty acid transport protein; medium chain acyl-CoA dehydrogenase; HMG-CoA synthase; acyl-CoA oxidase; peroxisomal emoyl-CoA hydratease/3-hydroxyacyl CoA dehydrogenase; peroxisomal 3-ketoacyl-CoA thiolase; acyl-CoA hydrolase; acyl-CoA thioesterase; cytochrome p450 4A1; cytochrome p450 4A2; cytochrome p450 4A3; cytochrome p450 4A6; delta-3-delta-3-delta-2 enoyl-CoA isomerase; acetyl CoA carboxylase; ATP citrate lyase; fatty acid synthase; flucose 6-phosphate dehydrogenase; glycerophosphate acyltransferase; malic enzyme; stearyl-CoA desaturase; hydroxysteroid dehydrogenase IV/bifunctional enzyme II; steroid 3a dehydrogenase; liver fatty acid binding protein; lipoprotein lipase; apolipoprotein A1; polipoprotein A2; apolipoprotein C3; 1-acylglycerophosphocholine acyltransferase; carnitine palmitoyl transferase-1; and heat shock protein GRP78.

In sone emvodiments, the plurality may include 3, 4, 5, 7, 10, 15, 20, 25, 30, 35 or more, or even all PPARα responsive nucleic acid sequences, or fragments thereof, disclosed herein.

Substrate Arrays for Identifying Agents and Pathologies Associated with PPARα Ligand Responsive Nucleic Acid Sequences The invention also includes a nucleic acid substrate array comprising one or more nucleic acid sequences. The nucleic acids can specifically identify one or more nucleic acid sequences encoding a polypeptide selected from the group consisting of: Carnitine/acyl carnitine carrier protein; Long chain acyl-CoA dehydrogenase; Short chain acyl CoA dehydrogenase; Long chain enoyl-CoA hydratase/3-hydroxyacyl-CoA dehydrogenase; Long chain ketoacyl-CoA thiolase; Propionyl-CoA carboxylase; Very long chain acyl-CoA synthetase; Carnitine octanoyl transferase; Epoxide hydrolase; Acetoacetyl-CoA thiolase; 8-aminolevulinate synthase; Porphobilinogen deaminase; Histidine decarboxylase; Cytochrome p450; phenobarbital inducible; Catalase; Dynein-like protein 3; Heat shock protein 60; Hydroxysteriod sulfotransferase; Cytochrome p450 M1; Androgen repressible liver protein SMP-2; UDP-glucosuronyl transferase-21; Metallothionein-1; Glutathione transferase Ya subunit; and SEQ ID NOS: 1–11.

The array may optionally contain include nucleic acids which identify one or more nucleic acids encoding long chain acyl CoA synthase; fatty acid transport protein; medium chain acyl-CoA dehydrogenase; HMG-CoA synthase; acyl-CoA oxidase; peroxisomal enoyl-CoA hydratase/3-hydroxyacyl CoA dehydrogenase; peroxisomal 3-ketoacyl-CoA thiolase; acyl-CoA hydrolase; acyl-CoA thioesterase; cytochrome p450 4A1; cytochrome p450 4A2; cytochrome p450 4A3; cytochrome p450 4A6; delta-3-delta-2 enoyl-CoA isomerase; acetyl CoA carboxylase; ATP citrate lyase; fatty acid synthase; flucose 6-phosphate dehydrogenase; glycerophosphate acyltransferase; malic enzyme; stearyl-CoA desaturase; hydroxysteroid dehydrogenase IV/bifunctional enzyme II; steroid 3a dehydrogenase; liver fatty acid binding protein; lipoprotein lipase; apolipoprotein A1; apolipoprotein A2; apolipoprotein C3; 1-acylglycerophosphocholine acyltransferase; carnitine palmitoyl transferase-1; and heat shock protein GRP78.

The nucleic acids in the array can identify the enumerated nucleic acids by e.g., having homologous nucleic acid sequences, such as oligonucleotide sequences, complementary to a portion of the recited nucleic acids.

Single Nucleotide Polymorphisms Associated with PPARα Ligand Responsive Genes

The invention also provides nucleic acid sequences nucleic acids containing polymorphisms associated with PPARα responsive genes. Eight genes, e.g., short chain acyl-CoA dehydrogenase, long chain ketoacyl-CoA thiolase, acetoacetyl-CoA thiolase, porphobilinogen deaminase, catalase, apolipoprotein A1, liver fatty acid binding protein, and heat shock protein 60 (See Table 1) were found to have single nucleotide polymorphisms. Five of these genes possess changes that altered amino acids (See Table 1; fourth column). Two amino acid changes (e.g., in acetoacetyl-CoA thiolase the change from Asp to Ile and in catalase the change from Pro to Leu) are nonconserved changes which could effect the structure and/or function of these proteins. The first column of Table 1 refers to the name of the gene discovered ("Gene responsive to PPARαL treatment in rat liver"), while the second column discloses the corresponding GenBank Accession Number ("Rat GenBank Accession Number"). The third column in the table refers to a CuraGen Corporation Accession Number of its proprietary human SeqCalling™ database ("Human SeqCalling™ Accession Number"). The fourth column shows -the location of the changed amino acid ("cSNP's change that alter amino acids"). The last column lists cSNPs that are not associated with amino acid changes ("cSNP's not associated with Amino Acid Changes").

TABLE 1

Single Nucleotide Polymorphisms (cSNP) in Genes encoding for proteins responsive to PPARαL

| Gene responsive to PPARαL treatment in rat liver | Rat GenBank Accession Number | Human SeqCalling ™ Accession Number | CSNP changes that alter amino acids | cSNP changes not associated with amino acid changes |
|---|---|---|---|---|
| Short chain acyl-CoA dehydrogenase | J05030 | gbh_m26393 | G657A (GLY-SER) | |
| Long chain ketoacyl-CoA thiolase | D16479 | gbh_d16481 | | C887G; G911A; G940A; C946T |
| Acetoacetyl-CoA thiolase | D13921 | gbh_d90228 | G1094A (VAL-MET) G1112A (ASP-ILE) G1214T (ALA-SER) | |
| Porphobilinogen deaminase | X06827 | gbh_x04217 | C558A (LEU-MET) | C539G; A594G; T636G |
| Catalase | M16670 | gbh_x04076 | C1110T (PRO-LEU) | T1237C |
| Apolipoprotein A1 | X00558 | gbh_x02162 | | A59T; A65G |
| Liver fatty acid binding protein | J00732 | gbh_m10050 | G322A (ALA-THR) | G26A |
| Heat shock protein 60 | D26494 | gbh_aj132085 | | T93C |

Catalase and porphobilinogen deaminase are both involved in free radical detoxification. Changes in these enzymes that affect the rate and efficiency of $O_2$ radical processing could be reflective of an individual patient's tolerance to this class of compounds. One of the major pathways of PPARαligand activity is through increased activation of acyl-CoA oxidase in peroxisomal fatty acid beta oxidation. The increased acyl-CoA activity results in one molecule of peroxide per fatty acid chain two-carbon unit processed, which is ultimately reduced by catalase. SNP's that enhance catalase activity may not be clinically apparent or assayable. Changes that impair catalase activity may predispose patients to an increased half-life of free radicals, exposing them to a higher risk of toxic damage.

Porphobilinogen deaminase efficiency affects the heme synthesis rate (heme is a cofactor found in all cytochromes and catalase). Reduced enzyme efficacy can thereby affect catalase function with similar consequences as outlined above. In our rodent model, several cytochromes were specifically upregulated by PPARαL. In the absence of adequate heme production, gene products resulting from upregulated transcription might be ineffective, thus reducing any metabolic effects gained by this upregulation. However, many of the observed rodent cytochrome upregulations have not been recapitulated in humans. Thus, the clinical significance of these changes may not be immediately apparent.

The term "polymorphism" refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Hybridizations are usually performed under stringent conditions, for example, at a salt concentration of no more than 1M and a temperature of at least 25.degree. C. For example, conditions of 5×SSPE (750 mM NaCl, 50 mM NaPhosphate, 5 mM EDTA, pH 7.4) and a temperature of 25.degree.–30.degree. C. are suitable for allele-specific probe hybridizations.

An isolated nucleic acid means an object species invention) that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

Analysis of Polymorphisms

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. Many of the methods described below require amplification of DNA from target samples. This can be accomplished by e.g., PCR. See generally, PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila et al., Nucleic Acids Res. 19, 4967

(1991); Eckert et al., PCR Methods and Applications 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR), (See Wu and Wallace, Genomics 4, 560 (1989), Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Natl. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Detection of Polymorphisms in Target DNA

There are two distinct types of analysis depending whether a polymorphism in question has already been characterized. The first type of analysis is sometimes referred to as de novo characterization. This analysis compares target sequences in different individuals to identify points of variation, i.e., polymorphic sites. By analyzing a groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The de novo identification of the polymorphisms of the invention is described in the Examples section. The second type of analysis is determining which form(s) of a characterized polymorphism are present in individuals under test. There are a variety of suitable procedures, which are discussed in turn.

1. Allele Specific Probes

The design and use of allele-specific probes for analyzing polymorphisms is described by e.g., Saiki el al., Nature 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some example of which are described by WO 95/11995 (incorporated by reference in its entirety for all purposes). One form of such arrays is described in the Examples section in connection with de novo identification of polymorphisms. The same array or a different array can be used for analysis of characterized polymorphisms. WO 95/11995 also describes subarrays that are optimized for detection of a variant forms of a precharacterized polymorphism. Such a subarray contains probes designed to be complementary to a second reference sequence, which is an allelic variant of the first reference sequence. The second group of probes is designed by the same principles as described in the Examples except that the probes exhibit complementarily to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarily. See Gibbs, Nucleic Acid Res. 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer. fee, e.g., WO 93/22456.

4. Direct-Sequencing

The direct analysis of the sequence of polymorphisms of the present invention can be accomplished using either the dideoxy chain termination method or the Maxam Gilbert method. See, Sambrook et al., Molecular Cloning, A Laboratory Manual (2nd Ed., CSHP, New York 1989); Zyskind et al., Recombinant DNA Laboratory Manual, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. See, e.g Erlich, ed., PCR Technology, Principles and Applications for DNA Amplification, (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

After determining polymorphic form(s) present in an individual at one or more polymorphic sites, this information can be used in a number of methods. Determination of which polymorphic forms occupy a set of polymorphic sites in an individual identifies a set of polymorphic forms that distinguishes the individual. See generally National Research Council, The Evaluation of Forensic DNA Evidence (Eds. Pollard et al., National Academy Press, DC, 1996). Since the polymorphic sites are within a 50,000 bp region in the human genome, the probability of recombination between these polymorphic sites is low. That low probability means the haplotype (the set of all 10 polymorphic sites) set forth in this application should be inherited without change for at least several generations. The more sites that are analyzed the lower the probability that the set of polymorphic forms in one individual is the same as that in an unrelated individual. Preferably, if multiple sites are analyzed, the sites are unlinked. Thus, polymorphisms of the invention are often used in conjunction with polymorphisms in distal genes. Preferred polymorphisms for use in forensics are diallelic because the population frequencies of two polymorphic forms can usually be determined with greater accuracy than those of multiple polymorphic forms at multi-allelic loci.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. In diallelic loci, four genotypes are possible: AA, AB, BA, and BB. If alleles A and B occur in a haploid genome of the organism with frequencies x and y, the probability of each genotype in a diploid organism are (See WO 95/12607):

Homozygote: $p(AA)=x^2$
Homozygote: $p(BB)=y^2=(1-x)^2$
Single Heterozygote: $p(AB)=p(BA)=xy=x(1-x)$
Both Heterozygotes: $p(AB+BA)=2xy=2x(1-x)$ The probability of identity at one locus (i.e, the probability that two individuals, picked at random from a population will have identical polymorphic forms at a given locus) is given by the equation:

$$p(ID)=x^2)^2+(2xy)^2+(y^2)^2.$$

These calculations can be extended for any number of polymorphic forms at a given locus. For example, the probability of identity p(ID) for a 3-allele system where the alleles have the frequencies in the population of x, y and z, respectively, is equal to the sum of the squares of the genotype frequencies:

$$p(ID)=x^4+(2xy)^2+(2yz)^2+(2xz)^2+z^4+y^4$$

In a locus of n alleles, the appropriate binomial expansion is used to calculate p(ID) and p(exc). The cumulative probability of identity (cum p(ID)) for each of multiple unlinked loci is determined by multiplying the probabilities provided by each locus:

$$\text{cum } p(ID)=p(ID1)p(ID2)p(ID3)\ldots p(IDn)$$

The cumulative probability of non-identity for n loci (i.e. the probability that two random individuals will be different at 1 or more loci) is given by the equation:

$$\text{cum } p(nonID)=1-\text{cum } p(ID).$$

If several polymorphic loci are tested, the cumulative probability of non-identity for random individuals becomes very high (e.g., one billion to one). Such probabilities can be taken into account together with other evidence in determining the guilt or innocence of the suspect.

The polymorphisms of the invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. For example, a heterozygous sickle cell mutation confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but hitherto unmapped genetic components. Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a .kappa.-squared test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

For animals and plants, correlations between characteristics and phenotype are useful for breeding for desired characteristics. For example, Beitz et al., U.S. Pat. No. 5,292,639 discuss use of bovine mitochondrial polymorphisms in a breeding program to improve milk production in cows. It was found that eleven of seventeen polymorphisms tested influenced at least one production trait. Bovines having the best polymorphic forms for milk production at these eleven loci are used as parents for breeding the next generation of the herd.

The previous section concerns identifying correlations between phenotypic traits and polymorphisms that directly or indirectly contribute to those traits. The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., Proc. Natl. Acad. Sci. (USA) 83, 7353–7357 (1986); Lander et al., Proc. Natl. Acad. Sci. (USA) 84, 2363–2367 (1987); Donis-Keller et al., Cell 51, 319–337 (1987); Lander et al., Genetics 121, 185–199 (1989)). Genes localized by linkage can be cloned by a process known as directional cloning. See Wainwright, Med. J. Australia 159, 170–174 (1993); Collins, Nature Genetics 1, 3–6 (1992) (each of which is incorporated by reference in its entirety for all purposes).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., Science 245, 1073–1080 (1989); Monaco et al., Nature 316, 842 (1985); Yamoka et al., Neurology 40, 222–226 (1990); Rossiter et al., FASEB Journal 5, 21–27 (1991).

Novel Rat Gene Fragments

A total of 11 novel rat gene fragments were isolated as PPARα-responsive. Three gene fragments represent transcripts homologous to known genes in rat or other species. Two gene fragments: (i) a 299 bp fragment with a 92% sequence identity to mouse carnitine acetyltransferase and (ii) a 371 bp fragment with an 88% sequence identity to rat acyl-CoA oxidase, also were determined to belong to PPARα-responsive metabolic pathways. A 467 bp fragment with a 90% sequence identity to human UDP-glucose pyrophosphorylase (an early step in glycogen synthesis) was found to be a novel PPARα-association. Eight gene fragments represent novel genes not previously characterized in other species.

Isolated Proteins and Polynucleotides

Accession numbers for GenBank database entries, providing the nucleotide and amino acid sequences for each clone and protein disclosed in the present application, are provided in FIG. 2. The actual nucleotide sequence of each clone can be determined by sequencing of the deposited clone in accordance with known methods. The predicted amino acid sequence can then be determined from such nucleotide sequence. The amino acid sequence of the protein encoded by a particular clone can also be determined by expression of the clone in a suitable host cell, collecting the protein and determining its sequence.

Within nucleotide sequences identified herein, potential open reading frames can be identified using the NCBI BLAST program ORF Finder available to the public. Because all known protein translation products are at least 60 amino acids or longer (Creighton, 1992, PROTEINS, 2nd Ed., W. H. Freeman and Co., New York), only those ORFs potentially encoding a protein of 60 amino acids or more are considered. If an initiation methionine codon (ATG) and a translational stop codon (TGA, TAA, or TAG) are identified, then the boundaries of the protein are defined. Other potential proteins include any open reading frames that extend to the 5' end of the nucleotide sequence, in which case the open reading frame predicts the C-terminal or core portion of a longer protein. Similarly, any open reading frame that extends to the 3' end of the nucleotide sequence predicts the N-terminal portion of a longer protein.

The following examples are presented in order to more fully illustrate the invention. The examples are not to be construed as limiting the scope of the invention defined by the appended claims.

EXAMPLES

Example 1

Rat Treatments

Harlan Sprague Dawley rats 10–14 weeks old were treated with oral tablet doses of: (i) PPARαL in an n-methylglucamine carrier twice daily (b.i.d) for a total of 3 days (3 rats total) or (ii) PPARαL in an n-methylglucamine carrier twice daily (b.i.d.) for a total of 3 days (3 rats total) or (iii) the n-methylglucamine carrier alone twice daily (b.i.d.) for a total of 3 days (3 rats total). On the fourth day, approximately 12 hours following the last dose of drug the animals were sacrificed. Liver and adipose tissue were harvested from all animals and snap frozen in liquid nitrogen.

Example 2

RNA Preparation

Total cellular RNA was isolated with Trizol (GIBCO-BRL; Baltimore Md.) using a one-tenth volume of bromochloropropane (Molecular Research Corp.; Cincinnati, Ohio) to facilitate phase separation. Contaminating DNA was removed by treatment with DNase I (Promega Biotech; Milwaukee, Wis.) in the presence of 0.01 M DTT (GIBCO-BRL; Baltimore, Md.) and 1 Unit/1 RNAsin (Promega Biotech; Milwaukee, Wis.). Following phenol/chloroform extraction, RNA quality was evaluated by spectrophotometry and formaldehyde agarose gel electrophoresis, and RNA yield was estimated by fluorometry with OliGreen® (Molecular Probes; Eugene, Oreg.). Poly(A)$^+$ RNA was prepared from 100 g of total RNA by use of oligo(dT) paramagnetic beads (PerSeptive Biosynthesis; Boston, Mass.), and quantitated with fluorometry.

Example 3
cDNA Synthesis

First strand cDNA was prepared from 1.0 g of poly(A)$^+$ RNA with 200 pmoles oligo(dT)$_{25}$V (where V=A, C or G) (PerSeptive Biosynthesis; Boston, Mass.) using 40 Units of SuperScript II reverse transcriptase (GIBCO-BRL; Baltimore, Md.). Second strand synthesis was performed at 16° C. for 2 hours following the addition of 10 Units of E. coli DNA ligase (GIBCO-BRL; Baltimore, Md.), 40 Units of E. coli DNA polymerase (GIBCO-BRL; Baltimore, Md.) and 3.5 Units of E. coli RNase H (GIBCO-BRL; Baltimore, Md.). Next, 1 1 of T$_4$ DNA polymerase (GIBCO-BRL; Baltimore, Md.) was then added, and incubation was continued at 16° C. for 5 minutes. The reaction was then treated with 5 Units of arctic shrimp alkaline phosphatase (USB; Chicago, Ill.) at 37° C. for 30 minutes and the cDNA was purified by phenol/chloroform extraction. The yield of cDNA was estimated using fluorometry.

Example 4
GENECALLING®

For all samples, triplicate GENECALLING® chemistry reactions were executed in parallel for each of 96 subsequence pairs. Restriction endonuclease digestion was performed in a reaction mix containing: 2.6 1 H$_2$O, 2 1 5.0 M betaine (Sigma; St. Louis, Mo.), 1 1 10x restriction endonuclease buffer, 0.8 1 10 mM dATP (Pharmacia; Newark, N.J.), 1 1 25% PEG (Fluka; St. Louis, Mo.), 0.2 1 of restriction enzyme 1 (NEB; Beverly, Mass., or Fermentas; Amherst, N.J.),0.2 1 restriction enzyme 2 and 1 I cDNA (1 ng/l). Digestion of cDNA is performed with the following thermocycler program: 30 minutes at 37° C., 22 minute ramp to 16° C., 1 hour at 16° C., 15 minutes at 37° C. and 20 minutes at 72° C. Following RE digestion, 0.2 1 of Ligase (BRL; Baltimore, Md.) with 1 1 Primer set 1 (Genosys; Woodlands, Tex. or Amitof, Boston, Mass.) and 1 1 Primer set 2 were added to the reaction mixture. The reactions were then maintained at 16° C. for the ligation of PCR primers. For PCR-based amplification, the following reagents were added: 2 1 10 mM dNTP mix (USB; Chicago, Ill.), 5 1 10x TB buffer (500 mM Tris pH 9.15, 160 mM (NH$_4$)$_2$SO$_4$, 20 mM MgCl$_2$), 0.25 U Klentaq (Invitrogen; Carlsbad, Calif.) :PFU (Stratagene; La Jolla, Calif.) (16:1 ratio), 32.75 1 H$_2$O. 20 cycles of amplification were then performed utilizing the following reaction conditions: an incubation comprising (30 seconds at 96° C., 1 second at 57° C. and 2 minutes at 72° C.) was followed with a 10 minute incubation at 72° C. PCR product purification was then performed using MPG streptavidin beads (CPG; Lincoln Park, N.J.). Following washing the beads twice with buffer 1 (3 M NaCl, 10 mM TRIS, pH 7.5, 1 mM EDTA), 20 1 of suspended beads were mixed with the PCR reaction product for 10 minutes at room temperature, separated with a magnet and washed once with buffer 2 (10 mM TRIS, pH 8.0, 1 mM EDTA). The beads were then dried and re-suspended in 3 1 of buffer 3 (80% formamide, 4 mM EDTA, 5% ROX-tagged molecular size standard (ABI; San Francisco, Calif.)). In addition, every other lane of the electrophoresis gel received 5% TAMRA (ABI; San Francisco, Calif.) as an inter-lane sample "bleed" control. Following denaturation at 96° C. for 3 minutes, the samples were loaded onto a 5% polyacrylamide, 6M urea, 1x TBE ultrathin gel (Long-Ranger, FMC; Philadelphia, Pa.) and electrophoresed for 60 minutes at 3500 V on a Niagara® electrophoresis instrument.

Example 5
Open Genome Initiative™ Software Gel Interpretation

The output of the electrophoresis instruments were interpreted using the internet-based Open Genome Initiative™ (OGI®) software suite. Gel images were visually-inspected for overall quality and each lane tracked to delineate the path of best fit. Each lane contained a GENECALLING® sample plus two sizing ladders (labeled with ROX and TAMRA fluorochrome) spanning the range from 50 bp to 500 bp. The molecular size "ladder" peaks provided a relationship between camera frames (typically collected at 1 Hz) and base pairs. After tracking, the lanes were extracted and the peaks in the molecular sizing ladder were resolved. Linear interpolation between the ladder peaks served to convert the GENECALLING® sample traces from frames to base pairs. Each trace was evaluated and ruled out for low signal-to-noise, poor peak resolution, absent ladder peaks and/or lane-to-lane bleed-through. Lanes which passed all of the criteria were submitted as point-by-point length verses amplitude addresses to the GENESCAPE® Oracle 8 database. Submitted traces were then organized by treatment group and fragmentation primers. The nine traces which corresponded to each treatment group/fragmentation pattern were then superimposed and were manually evaluated for intertrace alignment fidelity. Misaligned traces were rejected and excluded from subsequent analyses.

Example 6
Difference Calling

The expression difference analyses between each experimental state verses the appropriate experimental control were analyzed using the GENESCAPE® internet-based software package. To execute each pairwise analysis, GENESCAPE® accessed the Oracle database for all successfully aligned electrophoretic traces assigned to the experimental and control sample sets and applied a scaling algorithm for best-fit to normalize the traces of the experimental set versus that of the control. For each generated fragmentation pattern, the scaled traces were then compared on a point-by-point basis to define areas of amplitude difference which meet the minimum n-fold threshold selected for analysis. Once a region of difference was identified, the local maximum-for the corresponding traces of each set was then identified. The peak resolution was determined based upon the amplitude of the local maximum, the slope of the curve from baseline to the maximum and the area under this trace segment. All difference peaks with resolution thresholds exceeding an arbitrary value of 0.9 were stored as specific database addresses in the specified expression difference analysis. The list of detected differences was then presented as output over the internet-based GENESCAPE® interface.

Example 7
GENECALLING® Gene Assignment

For each comparison, the list of electrophoretic peaks representing expression differences was accessed through GENESCAPE®. Each difference fragment was then identified by the restriction enzyme pair used for fragmentation and by its length in base pairs. Restriction digestion fidelity ensured the exact identity of terminal 5'- and 3'- sequences. GENESCAPE® queried all species appropriate GenBank mRNA and EST entries to extract all sequences which could produce a restriction fragment with the selected RE pair±1.5 bp of the detected size. Following analysis of all expression differences, the lists generated for each fragment were merged with any GeneCalls which occurred for more than one fragment tallied. Each candidate GeneCall was queried against the set of RE pairs used in the comparison to determine the total number of predicted fragments between 40 bp and 450 bp each could generate. Each GeneCall was presented as the number of detected expression differences/ the number of predicted fragments and assigned a significance value based upon the ratio of detected/predicted (ire., weighted to eliminate bias when predicted $\leq 3$). The final GENECALLING® list was then outputted to GENESCAPE® sorted in descending order of significance.

Example 8

Gene Isolation

A total of 1 l of the GENECALLING® chemistry reaction containing the peak of interest was added to 3 l of 1× TAE buffer (Sigma; St. Louis, Mo.) and 1 l of gel loading dye (Elchrom Scientific; Lake Park, Fla.) and electrophoresed on an Elchrom Mini Gel (Elchrom Scientific; Lake Park, Fla.) at 55° C., 120 V for 30–150 minutes depending upon the size of the selected fragment. Following 15 minutes of ethidium bromide staining, the desired band length was excised from gel lane, placed into 10 mM $MgCl_2$, centrifuged at 3000 RPM for 5 minutes and heated to 65° C. for 30 minutes. Eluted fragments were then PCR-amplified using J23 and R23 PCR primers (Amitof; Boston, Mass.) and cDNA polymerase (Clontech; Palo Alto, Calif.) for 25 cycles of 30 seconds at 96° C., 60 seconds at 57° C., 2 minutes at 72° C. Subsequently, a 3 l aliquot was ligated to pCR2.1 cloning vector (Invitrogen; Carlsbad, Calif.) using the Fast-Link DNA ligation kit (Epicenter; Madison, Wis.). Vectors were electroporated into DH10B *E. coli* with 1.8 mV pulses and cells were plated on LB plates containing ampicillin, kanamycin, and X-gal (Northeast Laboratories; Waterville, Mass.). Colonies with inserts were selected for PCR amplification using 5 M betaine (Sigma; St. Louis, Mo.), DYN-A and DYN-RE primers (Amitof; Boston, Mass.) and Taq polymerase (Clontech; Palo Alto, Calif.) for 29 cycles of 1 second at 96° C., 1 minute at 57° C. and 1 minute at 72° C. The PCR reaction products were then submitted to sequencing for clone identification.

Example 9

Clone Sequencing 30 l of clone template were added to 6 l of SPRI beads (Bangs Laboratories; Fishers, Ind.) in 0.5 M EDTA pH 8.0 (Amresco; Solon, Ohio) and 30 l hybridization buffer (2.5 M NaCl, 20% PEG 8000 (Sigma; St. Louis, Mo.)) in 96-well plate format. Plates were shaken for 5 minutes at 600 rpm and then allowed to settle for 2 minutes on a magnet. The beads were washed a total of 4-times with 200 l of 70% EtOH (AAPER; Louisville, Ky.) and air dried for 2 minutes. 36 l of Nanopure water was then added to the beads. Plates were again shaken for 5 minutes at 600 rpm and the supernatant was collected for sequencing. 3 l of purified product was then transferred to: A (JOE-fluor), G (TAMRA-fluor), C (FAM-fluor) and T (ROX-fluor) reaction mixes (2 l DYEnamic Direct Cycle sequencing kit: DYEnamic-M13-40ET primers, premixed dGTP, Taq polymerase(Amersham Life Sciences; Piscataway, N.J.) and 1.8 l dNTP mix (Amersham Life Sciences; Piscataway, N.J.)) in 384-well formnat. Plates were then placed in a thermocycler for 15 cycles of: 5 seconds at 96° C., 10 seconds at 52° C. and 60 seconds at 72° C. Reactions were quenched at 4° C. For each template, the four reactions were pooled into one well of a 96-well plate and 65 l of 100% EtOH (AAPER; Louisville, Ky.) was added. Plates were chilled at 4° C. for 60 minutes and centrifuged at 4° C. for 30 minutes at 2000 rpm. The supernatant was removed and the plates were air dried to completion at 25° C. 3 l of formamide loading dye (Amersham; Piscataway, N.J.) was added to each well. In addition, 960 l of TAMRA-spiked loading dye (10:1 formamide; Amersham; Piscataway, N.J.): 55-mer TAMRA (Amitof; Boston, Mass.)) was added to selected wells for an electrophoresis quality control. The samples were electrophoresed in a 1× TBE Long Ranger (FMC; Philadelphia, Pa.) polyacrylamide gel on the AB1377 (ABI; San Francisco, Calif.) electrophoresis platform for 2.5 hours at 3000 volts. Gel images were resolved and interpreted by the OGI software interface. Images were quality-controlled for overall image fidelity and sequence quality of individual lanes. Lanes with truncated sequences, absent signals in one or more channels, bleed and primer dimerization were "failed" and precluded from further analysis. The sequences were subjected to BaseCalling and imported into GENESCAPE® were they were assigned to the difference peak corresponding to the specific sequence.

Equivalents

From the foregoing detailed description of the specific embodiments of the invention, it should be apparent that unique compositions and methods of use therefor in the treatment or cure of various diseases for novel and known genes modified by PPARαL have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of genes, compositions or methods of use therefor, or of specific diseases and disorders in which treatment may be mediated by such genes and/or compositions, is believed to be a matter of routine for a person of ordinary skill in the art with knowledge of the embodiments described herein.

What is claimed is:

1. A method of identifying a candidate therapeutic agent for a pathophysiology associated with a PPARα-mediated pathway, the method comprising:

(a) providing a cell comprising one or more nucleic acid sequences, wherein each nucleic acid sequence is selected from the group consisting of: SEQ ID NOS: 1–11;

(b) contacting said cell with a test agent; and (c) measuring expression of said nucleic acid sequences in said cell, wherein an alteration in expression of said genes in the presence of said test agent compared to expression of said genes in a control cell not exposed to said test agent indicates said test agent is a candidate therapeutic agent for a pathophysiology associated with a PPARα-mediated pathway.

2. A method of identifying a ligand for PPARα, said method comprising:

(a) providing a cell comprising one or more nucleic acid sequences, wherein each nucleic acid sequence is selected from the group consisting of: SEQ ID NOS: 1–11;

(b) contacting said cell with a test agent; and (c) measuring expression of said nucleic acid sequences in said cell, wherein an alteration in expression of said genes in the presence of said test agent compared to expression of said genes in a control cell not exposed to said test agent indicates the test agent is a ligand for PPARα.

3. A method of diagnosing a pathophysiology associated with a PPARα-mediated pathway in a subject, the method comprising:

(a) providing a cell from said subject, wherein said cell comprises one or more nucleic acid sequences selected from the group consisting of: SEQ ID NOS: 1–11; and (b) measuring expression of one or more of said nucleic acid sequences in said cell, wherein an alteration in expression of said genes as compared to the expression of said genes in a control cell indicates that said subject has a pathophysiology associated with a PPARα-mediated pathway.

4. A method of assessing the efficacy of a treatment for a pathophysiology associated with a PPARα-mediated pathway in a subject, said method comprising:

(a) providing a cell from a subject exposed to said treatment, wherein said cell comprises one or more nucleic acid sequences selected from the group consisting of: Seq. Nos. 1–11; and (b) measuring expression of said genes in said cell, wherein an alteration in expression of said nucleic acid in said cell compared to expression of said nucleic acid in a control cell not exposed to said treatment indicates said treatments is efficacious.

* * * * *

SEQUENCE LISTING

<160> NUMBER OF SEQ ID NOS: 11

<210> SEQ ID NO 1
<211> LENGTH: 274
<212> TYPE: DNA

<213> ORGANISM: Rattus sp.
<220> FEATURE:
<221> NAME/KEY: misc_feature
<222> LOCATION: (0)...(0)
<223> OTHER INFORMATION: f0h0_291.2
<221> NAME/KEY: misc_feature
<222> LOCATION: (21)...(274)
<223> OTHER INFORMATION: wherein n may be a or t or g or c

<400> SEQUENCE: 1

```
cctaggcatt tagcatccat ntactagagt ttaaagtntc ctgtgggttc ataaataata    60
gggaaggtat tttgatttaa tttanacagt tgatgcnant gananncthna agnntttnnc  120
nattanttta cacatagcnc gtggtanttg ggnnnattna ccnaatgnct tagancnttg   180
gnnaacacna ntantcangn ncacaaangt gtagnngnaa tttnantgna aacatnnatn  240
acnaaacnat gnttcnggng nttaccccaa tnnc                               274
```

<210> SEQ ID NO 2
<211> LENGTH: 146
<212> TYPE: DNA
<213> ORGANISM: Rattus sp.
<220> FEATURE:
<221> NAME/KEY: misc_feature
<222> LOCATION: (0)...(0)
<223> OTHER INFORMATION: b1i0_145
<221> NAME/KEY: misc_feature
<222> LOCATION: (31)...(31)
<223> OTHER INFORMATION: wherein n may be a or t or g or c

<400> SEQUENCE: 2

```
rccggtgcgt agtcttgggt gaaatgttaa ntatgcactg atcctcagga agttgggttc    60
gaaagggaga taaattacca aagtggtcca agaattgtat atgtggagaa acccatgtta  120
gagaaagaaa tcatatactc agatct                                         146
```

<210> SEQ ID NO 3
<211> LENGTH: 253
<212> TYPE: DNA
<213> ORGANISM: Rattus sp.
<220> FEATURE:
<221> NAME/KEY: misc_feature
<222> LOCATION: (0)...(0)
<223> OTHER INFORMATION: g0m0_173.1
<221> NAME/KEY: misc_feature
<222> LOCATION: (11)...(204)
<223> OTHER INFORMATION: wherein n may be a or t or g or c

<400> SEQUENCE: 3

```
tcatgaggcc nattcgctcc actgtggccc gcagccccg gaattcatca gtnagcgcct    60
tattcttggt gggttcaaag ctgggctgct ccggagctag ctctccaatc agaagagagt  120
tcatatactt tctcacaagg cccttgttaa tgtggaatgc cacaaaagga tccgtggcat  180
cctgaccagc gtagtggctg atgnaccggg agcctcccgg gtggtccgcg actgaagtcg  240
ctgatgttgt aca                                                       253
```

<210> SEQ ID NO 4
<211> LENGTH: 235
<212> TYPE: DNA
<213> ORGANISM: Rattus sp.
<220> FEATURE:
<221> NAME/KEY: misc_feature
<222> LOCATION: (0)...(0)
<223> OTHER INFORMATION: g1n0_234.3

<400> SEQUENCE: 4

```
tgtacagtta agtggaaatg agaactctgc actaagtaac tgcttccgt gaatgtgaag      60 aagattcttg caaagtggac tcaggacctt ggcactgtat ttgtaaaatg ataatgtgct    120
ttgagaaaac cttaggggga gggggatgaa agaaattaa agtggtaaaa caagacaaat    180
atgagtaaat gcctattttt actgtaacat taattatgtc taataaattt ctaga        235
```

```
<210> SEQ ID NO 5
<211> LENGTH: 280
<212> TYPE: DNA
<213> ORGANISM: Rattus sp.
<220> FEATURE:
<221> NAME/KEY: misc_feature
<222> LOCATION: (0)...(0)
<223> OTHER INFORMATION: y0i0_279.2

<400> SEQUENCE: 5
```

```
agatctttac tgagaagaaa tggctgctct ctaactggga gtagtgaaaa gtccaagggc     60
atctactttc tactcttaaa aagatgtgca ttttatattt taattagatc ctctacactc    120
taacattaac atatctgttc aaacttgtct agttgccaag tggcttgaga gtgttaagat    180
ttaaatcctt tttggagtat ctctgagagt agtctggaag caaaatgttc tcctctcagg    240
atgatgtcat ttgtgaagca gggaaacatg gagaactagt                         280
```

```
<210> SEQ ID NO 6
<211> LENGTH: 124
<212> TYPE: DNA
<213> ORGANISM: Rattus sp.
<220> FEATURE:
<221> NAME/KEY: misc_feature
<222> LOCATION: (0)...(0)
<223> OTHER INFORMATION: l0a0_123.9

<400> SEQUENCE: 6
```

```
ggtaccagga agctgtggaa aaggtgctgt taagatcatt ccccaatcag gtcttcagag     60
tccctgtgac cgacgcacag aacttcagct tctggcggtc caacagccca ggcgtgcgtc    120
cgga                                                                124
```

```
<210> SEQ ID NO 7
<211> LENGTH: 281
<212> TYPE: DNA
<213> ORGANISM: Rattus sp.
<220> FEATURE:
<221> NAME/KEY: misc_feature
<222> LOCATION: (0)...(0)
<223> OTHER INFORMATION: Rat EST H35859 (m0v0_283.6)

<400> SEQUENCE: 7
```

```
tcatgatgat agcctcctcc tccaggttct cccgaagaat ctgcagggtc ctgcggtcct     60
tctctgcctg gaggagtggc atgagggcga tcctggcctc caagtcctcg atcagcaggc    120
gcctacgctc ccggttccac ctcattattc tccagtagcc aaagatcaag gccccgatgc    180
ccaaagcaaa catgctgtat cccgacagtc ccggcggac aggtttccgc ttgtagtcga     240
tggggccgta gcccctggtg gggaattgtc ctgcttcacc t                       281
```

```
<210> SEQ ID NO 8
<211> LENGTH: 381
<212> TYPE: DNA
<213> ORGANISM: Rattus sp.
<220> FEATURE:
<221> NAME/KEY: misc_feature
<222> LOCATION: (0)...(0)
<223> OTHER INFORMATION: m0v0_382.0 (homologous to rat acyl-coA oxidase
```

```
      mRNA)
<221> NAME/KEY: misc_feature
<222> LOCATION: (284)...(365)
<223> OTHER INFORMATION: wherein n may be a or t or g or c

<400> SEQUENCE: 8
catgaacccc gacctgcgca aggagcgggc ctccgccacc ttcaatccgg agttgatcac    60
gcacatcttg gatggcagtc cggagaatac ccggcgccgt cgagaaattg agaacttgat   120
tctgaacgac ccagacttcc agcatgagga ctataacttc ctcactcgaa gaccagcgtt   180
atgaggtggc tgttaagaag agtgccacca tggtgaagaa gatgagggaa tatggcatct   240
cggaccctga agaaatcatg tggtttaaaa actctgtgca ccgncggcat cctgagcctt   300
tggaccttca cttgggcatg ttcctaccca ccttgcttnc cngnccancg gagagnngca   360
ggagngcttc ttcatgccgg c                                              381

<210> SEQ ID NO 9
<211> LENGTH: 298
<212> TYPE: DNA
<213> ORGANISM: Rattus sp.
<220> FEATURE:
<221> NAME/KEY: misc_feature
<222> LOCATION: (0)...(0)
<223> OTHER INFORMATION: m0v0_298.5 (homolog to mouse mRNA for carnitine
      acetyltransferase)

<400> SEQUENCE: 9
gccggccaga tgcttcatgg tggtggcagc aagttcaaca gtggcaaccg ctggttcgac    60
aagacactgc agtttattgt ggcagaagat ggctcctgtg ggatggttta tgaacatgca   120
gctgcagaag ggccccccat tgtcgctctt gtggaccatg tcatggagta tacaaagaag   180
cctgaacttg tgcggtcccc tatggtaccc ctgcctatgc ccaagaagct gcggttcaac   240
atcacacctg agatcaagaa tgacatagag aaggccaaac agaacatcag catcatga    298

<210> SEQ ID NO 10
<211> LENGTH: 420
<212> TYPE: DNA
<213> ORGANISM: Rattus sp.
<220> FEATURE:
<221> NAME/KEY: misc_feature
<222> LOCATION: (0)...(0)
<223> OTHER INFORMATION: m0r0_161.2
<221> NAME/KEY: misc_feature
<222> LOCATION: (375)...(375)
<223> OTHER INFORMATION: wherein n may be a or t or g or c

<400> SEQUENCE: 10
agttttgtaa acagctaatt ttattccttg ataccaattg gttgttcatg atacatactt    60
ttctgcaaga aggcaatgaa tgaaataaag gcatagaggg gaaattgggg aaaaaccaca   120
atgtagtagg atgtcactta attaaactcg tacttgattg gctagttgtt ttagttacaa   180
tttcaagtct tatagataca gaattctact ttttttccag aacaaacata tatgtcctta   240
aagacagtgg gggagacaac agatttttaa ctgctgagct tcttacttct aaggagaaca   300
gtcaacattg ttacttcttg tccttcacag tctggaattc atgtgggtca ttagcttctc   360
caatttgatt gctanggcta tgtttccttt aatcttcaac tttcctgaca taaatgccat   420

<210> SEQ ID NO 11
<211> LENGTH: 467
<212> TYPE: DNA
<213> ORGANISM: Rattus sp.
<220> FEATURE:
```

-continued

```
<221> NAME/KEY: misc_feature
<222> LOCATION: (0)...(0)
<223> OTHER INFORMATION: 10n0_235.7 (homolog to human uridine
      diphosphoglucose pyrophosphorylase mRNA)
<221> NAME/KEY: misc_feature
<222> LOCATION: (10)...(149)
<223> OTHER INFORMATION: wherein n may be a or t or g or c

<400> SEQUENCE: 11
aaagctatgn tctcaagatg ggggcttctc agttccaaga gggtcattct ccaagaacta        60
gaattatctg tgaagaaaga attagaaaaa atacttacca cagcaacctc acatgagttt       120
gagcacacta agaaagatct tgnatggatt tcggaagcta tttcacagat ttttgcaaga       180 aaagggcct tctgtagact ggggtaaaat ccagagactc cggaagattc gattcaaccc        240
tatgaaaaga taaaggccag aggcttgcct gataacatat cttctgtgtt gaacaaactg      300
gtggtagtga aactcaatgg tggtttggga accagcatgg gctgcaaagg ccctaaaagt       360
ctgattggtg taagaaatga gaatacctttt ttggatctaa ccgttcagca aattgaacat     420
ctgaacaaaa cctataatac agatgtcccg ctcgtattaa tgaattc                    467
```